(12) United States Patent
Menon et al.

(10) Patent No.: US 10,373,718 B2
(45) Date of Patent: Aug. 6, 2019

(54) DECISION SUPPORT TOOL FOR STROKE PATIENTS

(71) Applicants: Bijoy Menon Professional Corporation, Calgary, Alberta (CA); M and S Goyal Professional Corporation, Calgary, Alberta (CA); Supriya M Goyal Professional Corporation, Calgary, Alberta (CA); Ting Yim Lee, London, Ontario (CA); Michael D. Hill Professional Corporation, Calgary, Alberta (CA); Andrew Demchuk Professional Corporation, Calgary, Alberta (CA)

(72) Inventors: Bijoy K. Menon, Calgary (CA); Mayank Goyal, Calgary (CA); Ting Yim Lee, London (CA); Seonghwan Ahn, Gwangju (KR); Andrew Michael Demchuk, Calgary (CA); Michael Douglas Hill, Calgary (CA)

(73) Assignees: Bijoy Menon Professional Corporation, Calgary (CA); M and S Goyal Professional Corporation, Calgary (CA); Supriya M Goyal Professional Corporation, Calgary (CA); Ting Yim Lee, London (CA); Michael D. Hill Professional Corporation, Calgary (CA); Andrew Demchuk Professional Corporation, Calgary (CA)

( * ) Notice: Subject to any disclaimer, the term of this patent is extended or adjusted under 35 U.S.C. 154(b) by 619 days.

(21) Appl. No.: 14/955,947

(22) Filed: Dec. 1, 2015

(65) Prior Publication Data

US 2016/0180042 A1    Jun. 23, 2016

Related U.S. Application Data

(60) Provisional application No. 62/086,077, filed on Dec. 1, 2014.

(51) Int. Cl.
*G16H 50/20* (2018.01)
*A61B 6/00* (2006.01)
(Continued)

(52) U.S. Cl.
CPC ........... *G16H 50/20* (2018.01); *A61B 5/0042* (2013.01); *A61B 5/02042* (2013.01);
(Continued)

(58) Field of Classification Search
CPC ...... G16H 50/20; G16H 50/30; G06F 19/345; G06F 19/321; A61B 5/02042;
(Continued)

(56) References Cited

U.S. PATENT DOCUMENTS

| 8,792,701 B2 | 7/2014 | Djeridane et al. |
| 8,837,800 B1 | 9/2014 | Bammer et al. |

(Continued)

FOREIGN PATENT DOCUMENTS

| FR | 2953309 A1 | 3/2011 |
| FR | 2952452 A1 | 5/2011 |

(Continued)

OTHER PUBLICATIONS

Yang, et al., "Multiphase CT Angiography versus Single-Phase CT Angiograpy: Comparison of Image Quality and Radiation Dose", AJNR, Aug. 2008, pp. 1288-1295, vol. 29, www.ajnr.org. (Year: 2008).*

(Continued)

*Primary Examiner* — Jonathan Durant
*Assistant Examiner* — Gregory D. Moseley
(74) *Attorney, Agent, or Firm* — Whitmyer IP Group LLC

(57) ABSTRACT

An automated system and method for assisting in decision making for the treatment of stroke patients is provided, and specifically for assisting a physician whether the patient should be administered a drug or transferred to another (Continued)

hospital to undergo an endovascular thrombectomy procedure. A variety of factors are input into the system with limited human intervention and a tool automatically determines the probability of whether the patient will have a better outcome if transferred or not. The factors include clinical factors, imaging factors and time to transfer factors. The tool includes processes for automatically determining several imaging factors, including the determination of clot length, collateral blood flow, the presence of forward blood flow within and around the clot, and the clot permeability. The tool has capability to continuously update the treatment protocol and other output results using current clinical, health system or other relevant information or feedback.

19 Claims, 23 Drawing Sheets

(51) Int. Cl.
| | | |
|---|---|---|
| | A61B 5/00 | (2006.01) |
| | A61B 8/08 | (2006.01) |
| | G06F 19/00 | (2018.01) |
| | A61B 5/02 | (2006.01) |
| | G16H 50/30 | (2018.01) |
| | A61B 6/03 | (2006.01) |
| | A61B 5/055 | (2006.01) |
| | A61B 5/053 | (2006.01) |

(52) U.S. Cl.
CPC ............ A61B 5/4064 (2013.01); A61B 6/501 (2013.01); A61B 8/0808 (2013.01); G06F 19/321 (2013.01); G16H 50/30 (2018.01); A61B 5/055 (2013.01); A61B 5/0535 (2013.01); A61B 6/032 (2013.01); A61B 8/488 (2013.01); A61B 2576/00 (2013.01); A61B 2576/026 (2013.01); G01N 2800/2871 (2013.01); G06T 2207/30004 (2013.01)

(58) Field of Classification Search
CPC ..... A61B 5/4064; A61B 8/0808; A61B 6/501; A61B 5/0042; A61B 2576/026; A61B 2576/00; A61B 6/032; A61B 5/055; A61B 8/488; A61B 5/0535; G06T 2207/30004; G01N 2800/2871

See application file for complete search history.

(56) References Cited

U.S. PATENT DOCUMENTS

| | | | |
|---|---|---|---|
| 2004/0106864 A1 | 6/2004 | Rose et al. | |
| 2006/0102502 A1* | 5/2006 | Biscotti | B65D 85/24 206/363 |
| 2007/0167757 A1 | 7/2007 | Menezes et al. | |
| 2009/0129649 A1 | 5/2009 | Djeridane | |
| 2011/0313783 A1* | 12/2011 | Sacco | G06Q 50/22 705/2 |
| 2012/0020538 A1 | 1/2012 | Weiss | |
| 2012/0094266 A1 | 4/2012 | Lynch et al. | |
| 2012/0114205 A1 | 5/2012 | Tang et al. | |
| 2013/0266201 A1 | 10/2013 | Pautot | |
| 2013/0296720 A1* | 11/2013 | McKinley | A61B 5/0205 600/484 |
| 2014/0128707 A1* | 5/2014 | Bakker | G06F 19/3456 600/369 |
| 2014/0180146 A1 | 6/2014 | Nicoli | |
| 2014/0219532 A1 | 8/2014 | Pautot | |
| 2015/0227710 A1* | 8/2015 | Pappada | G06Q 50/22 705/2 |
| 2015/0228076 A1* | 8/2015 | Mouridsen | G16H 50/30 382/131 |

FOREIGN PATENT DOCUMENTS

| | | |
|---|---|---|
| WO | 2011064512 A1 | 6/2011 |
| WO | 2011068475 A1 | 6/2011 |
| WO | 2014036638 A1 | 3/2014 |
| WO | 2014053796 A1 | 4/2014 |
| WO | 2015039249 A1 | 3/2015 |

OTHER PUBLICATIONS

Chung-Hun J. Sun et al. Door-to-Puncture: A Practical Metric for Capturing and Enhancing System Processes Associated With Endovascular Stroke care, Preliminary Results From the Rapid Reperfusion Registry, Journal of the American Heart Association, 2014, pp. 1-9, American Heart Association, Inc.

Mayank Goyal et al., Acute stroke, Bayes' theorem and the art and science of emergency decision-making, Journal of Neurointerventional Surgery, Dec. 2013, pp. 1-4, BMJ Publishing Group.

Mayank Goyal et al. Consistently Achieving Computed Tomography to Endovascular Recanalization <90 Minutes: Solutions and Innovations, Stroke, Oct. 28, 2015, pp. 1-5, American Heart Association, Dallas, TX.

InTouch Health and iSchemaView Partner to Improve Care for Stroke Victims, Jul. 23, 2015 Business Wire.

Olea Medical to join Toshiba Medical Systems, BioSpectrum India (via HT Media Ltd.), Oct. 16, 2015.

Deal snapshot: Toshiba Medical Systems Buys French Medical Imaging Software Firm Olea, M&A Navigator, Oct. 13, 2015.

Olea Medical to Join Toshiba Medical Systems Corporation Group, Business Wire, Oct. 13, 2015.

Toothbrush Innovator Kolibree Completes First Round of Funding to Support Rapid Growth in U.S. Dental Market, Business Wire, Jun. 10, 2015.

Maru Boesen et al., Time-Dependent CT Perfusion Threshold for Triage of Patients with Acute Ischemic Stroke, Stroke Manuscript Submission and Peer Review System, American Heart Association.

Mayank Goyal, Analysis of workflow and time to treatment on thrombectomy outcome in the ESCAPE randomized controlled trial, version 5, pp. 1-25.

Patent Cooperation Treaty, Written Opinion and International Search Report dated Feb. 8, 2016, issued on PCT Application No. PCT/CA2015/000589.

Olvert A. Berkhemer, A Radomized Trial of Intraarterial Treatment for Acute Ischemic Stroke, The New England Journal of Medicine, Jan. 1, 2015, pp. 11-20, vol. 372 No. 1, The Massachusetts Medical Society.

Bruce C. V. Campbell, Endovascular Therapy for Ischemic Stroke with Perfusion-Imaging Selection, The New England Journal of Medicine, Mar. 12, 2015, pp. 1009-1018, The Massachusetts Medical Society.

Kohsuke Kudo, Differences in CT Perfusion Maps Generated by Different Commercial Software: Quantitative Analysis by Using Identical Source Data of Acute Stroke Patients, Radiology, Jan. 2010, vol. 254: No. 1, The Radiology Society of North America.

Bijoy K. Menon, Multiphase CT Angiography: A New Tool for the Imaging Triage of Patients with Acute Ischemic Stroke, Radiology, 2015, Volumber 000: No. 0, The Radiology Society of North America.

Laura Landro, A Fast Track to Treatment for Stroke Patients, The Wall Street Journal, Mar. 2, 2015, Dow Jones Company.

Jonathan Emberson et al., Effect of treatment delay, age, and stroke severity on the effects of intravenous thrombolysis with alteplace fr acute isochaemic stroke: a meta-analysis of individual patient data from randomised trials, Lancet, Nov. 29, 2014.

Bijoy K. Menon et al., Role of Imaging in Current Acute Ischemic Stroke Workflow for Endovascular Therapy, Stroke, May 5, 2015, American Heart Association, Dallas, TX.

Nandavar Shobha et al., Measurement of Length of Hyperdense MCA Sign in Acute Ischemic Stroke Predicts Disappearance after IV tPA, Journal of Neuroimaging, Jan. 1, 2015, vol. 24 No. 1, pp. 7-10, American Society of Neuroimaging.

(56) References Cited

OTHER PUBLICATIONS

Bijoy K. Menon et al., Aspects and Other Neuroimagning Scores in the Triage and Prediction of Outcome in Acute Stroke Patients, Neuroimaging Clinics of North America, 2011, pp. 407-423, Elsevier Inc.

S.M. Mishra et al. Early Reperfusion Rates with IV pTA Are Determined by CTA Clot Characteristics, American Journal of Radiology, Jul. 24, 2014, pp. 1-8, American Society of Neuroradiology.

Leanne K. Casaubon et al., Canadian Stroke Best Practice Recommendations: Hyperacute Stroke Care Guidelines, Update 2015, International Journal of Stroke, 2015, pp. 1-17, World Stroke Organization.

Bijoy K. Menon et al., Assessment of leptomeningeal collaterals using dynamic CT angiography in patients with acute ischemic stroke, Journal of Cerebral Blood Flow and Metabolism, Nov. 2015, pp. 1-7, The International Society of Cerebral Blood Flow and Metabolism.

Seong Hwan Ahn et al., Occult Anterograde Flow Is in Underrecognized But Curcial Predictor of Early Recanalization With Intravenous Tissue-Type Plasminogen Activator, Stroke, Apr. 2015, pp. 1-8, American Heart Association, Dallas, TX.

Mayank Goyal et al., Randomized Assessment of Rapid Endovascular Treatment of Ischemic Stroke, The New England Journal of Medicine, Feb. 11, 2015, pp. 1-15, Massachusetts Medical Society.

\* cited by examiner

| VARIABLES | ODDS RATIO | 95% CI | P VALUE |
|---|---|---|---|
| GROUP 1 (RETROGRADE FLOW AND T0 TIME DIFFERENCE OVER 2 SECONDS)* | 1 | – | – |
| GROUP 2 (RETROGRADE FLOW OR T0 TIME DIFFERENCE OVER 2 SECONDS) | 2.15 | 0.43-10.72 | 0.35 |
| GROUP 3 (ANTEGRADE FLOW AND T0 TIME DIFFERENCE BELOW 2 SECONDS) | 12.15 | 2.05-71.91 | 0.006 |
| WHITE BLOOD CELL COUNT (FOR EVERY 1000 CELLS PER ml) | 0.76 | 0.59-0.98 | 0.037 |
| AGE (IN YEARS) | 0.98 | 0.94-1.03 | 0.526 |

*REFERENCE GROUP

FIG. 5

DECISION SUPPORT TOOL FOR STROKE PATIENTS

CROSS REFERENCE TO RELATED APPLICATION

This application claims priority to U.S. Provisional Application No. 62/086,077 filed Dec. 1, 2014 entitled SYSTEMS AND METHODS FOR ASSISTING IN DECISION MAKING AND TRIAGING FOR ACUTE STROKE PATIENTS, which is hereby incorporated by reference.

FIELD

Embodiments described herein relate generally to stroke patients and their physicians or healthcare providers, and more specifically to systems and methods to assist physicians or healthcare providers in decision making for patients who are experiencing or have experienced acute ischemic stroke.

BACKGROUND

When a physician or healthcare provider initially suspects that a patient has had a stroke, the physician will undertake a number of steps to verify the diagnosis. In initially diagnosing whether the patient has suffered a hemorrhagic or an ischemic stroke, the physician may have initially completed brain imaging using an image scanner. This initial high level diagnosis is important in considering treatment options and in particular whether or not to administer thrombolytic drugs, which may be referred to as a clot dissolving or busting drug. Until recently, the thrombolytic drug referred to as a pharmacological tissue plasminogen activator (tPA) has been the only non-surgical standard of care for treating patients with acute ischemic stroke. There are several different types of tPA which is a recombinant human protein. Alteplase is the generic name of the marketed version of tPA that is used to treat stroke. As is known, tPA works by breaking up the thrombus or blood clot blocking blood flow to the brain that had caused the stroke. While this non-surgical treatment is highly effective in many scenarios, the drug may not succeed in dissolving the thrombus when the thrombus itself is either too large and/or the thrombus does not have the porosity to enable effective and timely penetration of the drug within the thrombus. In addition, tPA cannot be given to people who are taking blood thinners or have had recent surgery or have another of several medical contraindications to thrombolytic therapy.

It is in this context that recent stroke trials have shown efficacy of another treatment, namely the use of various endovascular techniques and specifically, the use of catheter systems to remove a thrombus from within the brain arteries. Endovascular therapy is highly efficacious, however it entails a very high level of expertise from the surgical teams as well as the supporting infrastructure. As such, it is limited to a relatively small number of tertiary care hospitals across the world.

As a result, given the generally resource intensive nature of endovascular therapy and the required skill levels of the physicians, these procedures may generally only be available in a relatively low number of large hospitals.

Stroke, however, is a common disease with a wide range of severity. That is, minor strokes may require no treatment whereas non-fatal severe strokes can result in a wide range of outcomes for the patient and a wide range of disabilities. As such, the ultimate outcome of the patient can be affected by a number of factors.

Importantly, many stroke patients will be taken to hospitals near their community where endovascular therapy is unavailable. Some of these patients may benefit from thrombolytic drugs (e.g. alteplase), while others may need to be transferred to a larger tertiary hospital in order to benefit from endovascular therapy.

Decisions on whether to transfer patients need to be made quickly, as every minute counts in cases where endovascular therapy is the preferred treatment. That is, in a typical acute ischemic stroke case where affected areas of the brain are at risk of dying, every minute until reperfusion the brain loses on average of 1.9 million neurons, 14 billion synapses and 7.5 miles of myelinated fibers. On the other hand, in cases where affected areas of the brain are already irreversibly infarcted, decisions have to be appropriate and correct to avoid patients being transferred to larger hospitals where endovascular therapy is unlikely to produce a better outcome for the patient.

Currently, the expertise needed to make these triaging decisions is unavailable in community hospitals. As a result, physicians in these community hospitals may make decisions that result in significant costs in unnecessarily transferring patients to larger centers and incurring additional diagnostic and treatment costs at these larger centers when the treatment outcome is unlikely to have been improved. On the other hand valuable time may be lost in decision-making and other delays in transfer of patients at the community hospitals who may actually benefit from the transfer to a tertiary care hospital for endovascular thrombectomy.

SUMMARY

In an aspect of embodiments described herein, there is provided automated decision support tools, systems and methods for determining whether a stroke patient should be transferred from a first hospital (i.e. a community hospital) to a second larger hospital (i.e. a tertiary hospital) where endovascular therapy is available, or whether a stroke patient should be kept at the first hospital. An example system may assist in determining if transfer is going to be beneficial or futile. In some embodiments, the system may do so by determining if the thrombolytic drug (administered at the community hospital) is going to be successful in dissolving the thrombus or not and by determining the amount of brain that is already irreversibly infarcted or is likely to be irreversibly infarcted in the time it takes for the transfer from the community hospital to the tertiary hospital. The system may also take into account practical considerations, such as distance from the tertiary hospital, age of the patient (date or range, for example) and severity of stroke symptoms, for example, to provide tangible output results in helping the physician make a transfer decision. The system may use efficient processing techniques to generate output results. In some embodiments, input factors considered by the system for assisting a physician's decision-making regarding stroke patients include the fundamental severity of the stroke, the specific treatment received as well as determining estimates of various time components contributing to the treatment including time passage from initial symptom onset to mobility of the patient for treatment, travel time to a care facility, initial diagnosis at the care facility, imaging time, additional diagnosis time of the extent and severity of the stroke, time to administration of drugs and/or the initiation of endovascular therapy, and so on.

In another aspect, there is provided a method for a decision support tool for evaluating a patient suffering from acute stroke.

The method may involve receiving patient clinical information and patient brain scan electronic images at a processor; generating, at the processor, a patient brain imaging profile using the patient clinical information and the brain scan electronic images, the imaging profile identifying a quantity and eloquence of brain tissue that is irreversibly infarcted, an estimated rate or quantity of patient brain tissue that become irreversibly infarcted at a future time, a thrombus morphology associated with an estimate of a thrombus dissolving at the future time, and an estimated collateral blood flow; determining an estimated transport time to transfer the patient to a treatment facility and an estimated treatment time for receiving reperfusion at the treatment facility; dynamically determining, using the processor, a patient assessment profile by: processing the patient clinical information, the patient brain imaging profile, the estimated transport time, and the estimated treatment time to generate input data values; dynamically deriving weighting factors as an assessment of importance or relevance of the input data values and assigning the weighting factors to the input data values; deriving as output data values for the patient assessment profile using the input data values and the weighting factors, the output data values being a probability of an expert treatment decision for transferring the patient to the treatment facility and providing the reperfusion at the treatment facility, and a visual representation of the thrombus morphology, the estimated collateral blood flow, and an estimated quantity of brain tissue that will likely become irreversibly infarcted after the estimated transport time and/or the estimated treatment time; and outputting the output data values as clinical decision support information for triggering display on a display device, for storing on a storage device, or for transmission to another processor using a transmitter. The eloquence may define or reference how important the function of the brain tissue is. The method may involve determining collateral blood flow using one or more $T_{max}$ values as described herein to provide various visual representations of the estimates. The processor may be configured with various threshold values for the probability of the expert treatment decision that may be physician or health care facility dependent, where each threshold value may trigger an action or predefined output result. For example, a probability of the expert treatment decision over 80% may trigger a transport action.

In some embodiments, the method may involve determining that the patient is already at the treatment facility and updating the visual representation with the estimated quantity of brain tissue that will likely become irreversibly infarcted after the estimated treatment time for receiving reperfusion.

In some embodiments, the method may involve determining or receiving a patient clinical data profile identifying an age or age range for the patient and a stroke severity, the stroke severity defined on a scale of mild, moderate and severe or based on physician heuristics, and determining the patient assessment profile using the patient clinical data profile as input to the system model.

In some embodiments, the method may involve determining the time elapsed since the onset of stroke symptoms as an additional input data value for the patient assessment profile.

In some embodiments, the method may involve determining the patient's pre-morbid status, general health and co-morbidities as an additional input data values for the patient assessment profile.

In some embodiments, the method may involve determining the patient's advanced directives as an additional input data values for the patient assessment profile.

In some embodiments, the method may involve determining current medications and/or medical history of patient that significantly influence decision making as an additional input data value for the patient assessment profile, including blood thinners and recent surgery.

In some embodiments, the method may involve providing an imaging interface to connect to an imaging device to receive the brain scan image files, the imaging device selected from the group consisting of a scanner, a picture archiving communication system network, and a cloud image storage device.

In some embodiments, the method may involve determining the estimated transport time and the estimated treatment time comprises determining a required treatment for the patient and identifying one or more available treatment facilities based on available treatment services and equipment, available treatment times, available transportation type and the required treatment of the patient. The method may also involve determining other time estimates, such as the estimated transit time of the cerebral perfusion image or other types of images.

In some embodiments, the method may involve continuously updating the patient assessment profile using a feedback loop based on additional input data values including configurations for the current physician and health system, additional available patient and health system data, changing configurations for the physician and health care facility, updates for the one or more weighting factors, control commands received from a display device displaying the visual representation.

In some embodiments, the method may involve constructing and continuously validating the patient assessment profile and the input data values using current and future clinical trial datasets.

In some embodiments, the method may involve constructing and continuously validating the patient assessment profile by receiving additional data and results on adjuvant therapies including neuro-protection and augmented thrombolytic techniques to change physician and health system heuristics.

In some embodiments, the method may involve receiving threshold data for a health care provider to update and customize the patient assessment profile, the weighting factors, and the input data values for the health care provider, the health care data including number of treatment centers providing endovascular treatment, staff availability, and other current health care metrics.

In some embodiments, the method may involve determining the patient assessment profile by determining a rate of brain tissue death using collateral assessment on various image scans, such as computed tomography (CT) angiography (CTA), CT Perfusion (CTP), Magnetic resonance imaging (MRI) or a combination of thereof.

In some embodiments, the method may involve the likelihood of the thrombus dissolving within a specific future time as determined by one or more techniques of measuring thrombus morphology such as a size of the thrombus, length of the thrombus, surface area of the thrombus, volume of the thrombus, and permeability to blood flow of the thrombus.

In some embodiments, the method may involve determining a likelihood of the thrombus dissolving with administration of a thrombolytic drug using the thrombus morphology and the collateral blood flow, the patient treatment protocol indicating the likelihood of the thrombus dissolving with administration of the thrombolytic drug.

In some embodiments, the method may involve the output data values of the patient assessment profile to indicate a comparison between risks of the administration of a thrombolytic drug and risks of endovascular treatment, the risks including a bleeding risk and other potentially major risks associated with thrombolytic drug administration and a treatment risk of not being able to administer the endovascular treatment or not successfully providing the endovascular treatment.

In some embodiments, the method may involve the collateral blood flow as determined using multi-phase CTA (mCTA), $T_0$ and $T_{max}$ values.

In some embodiments, the method may involve the patient brain electronic images as one or more imaging modalities selected from the group consisting of CT scan, multi-phase CTA, and CT perfusion, MRI, Trans Cranial Doppler (TCD), ultrasound (US), Electrical Impedance Plethysmography (EIS) and other imaging modalities.

In some embodiments, the patient treatment protocol is selected from the group consisting of: transferring the patient to the treatment facility for treatment with endovascular therapy; transferring the patient to the treatment facility for direct treatment without additional or repeating brain scans; retaining the patient at an initial treatment facility for treatment with a thrombolytic drug; and retaining the patient at the initial treatment facility.

In some embodiments, the method may involve receiving additional patient, clinical and imaging data for stroke patients; updating the input data values using the additional patient, clinical and imaging data for stroke patients; and updating patient treatment protocol using machine learning and the additional patient data, health system data, the updating by applying additional weighting factors to the updated input data values.

In some embodiments, the treatment protocol provides a visual representation as a time-based a Computed Tomography Perfusion (CTP) map interface for display on the display device. The map interface may receive control commands and other feedback to re-generate or update the treatment protocol based on the displayed visual representation.

In some embodiments, treatment protocol indicates one or more of an automated prediction of thrombus lysability using the thrombus morphology, an automated quantitation of collateral status on a CTP map and on multi-phase CTA and an automated assessment of severe hypoattenuation on non-contrast CT.

In another aspect there is provided a decision support computing tool. The tool may have an image interface to receive patient brain electronic images. The tool may have a processor to: receive patient clinical information; generate a patient brain imaging profile using the patient brain scan electronic images and the patient clinical information, the imaging profile identifying a quantity and eloquence of brain tissue that is irreversibly infarcted, an estimated rate or quantity of patient brain tissue that will become irreversibly infarcted at a future time, a thrombus morphology associated with an estimate of a thrombus dissolving at the future time, and an estimated collateral blood flow; determine an estimated transport time to transfer the patient to a treatment facility and an estimated treatment time for receiving reperfusion at the treatment facility; and dynamically determine a patient assessment profile by: processing the patient clinical information, the patient brain imaging profile, the estimated transport time, and the estimated treatment time to generate input data values; dynamically deriving weighting factors as an assessment of importance or relevance of the input data values and assigning the weighting factors to the input data values; deriving output data values for the patient assessment profile using the input data values and the weighting factors, the output data values being a probability of an expert treatment decision for transferring the patient to the treatment facility and providing the reperfusion at the treatment facility, and a visual representation of the thrombus morphology, the estimated collateral blood flow, and an estimated quantity of brain tissue that will become irreversibly infarcted after the estimated transport time and/or the estimated treatment time. The tool may have a display device to display the patient treatment protocol as clinical decision support information including the visual representation. The tool may have a network interface to provide the output data values for transmission or storage.

In some embodiments, the processor determines that the patient is already at the treatment facility and triggers a graphical update to the visual representation with the estimated quantity of brain tissue that will likely become irreversibly infarcted after the estimated treatment time for receiving reperfusion.

In some embodiments, the processor determines or receives a patient clinical data profile identifying an age or age range for the patient and a stroke severity, the stroke severity defined on a scale of mild, moderate and severe or based on physician heuristics, and determine the patient assessment profile using the patient clinical data profile.

In some embodiments, the processor receives or otherwise determines the time elapsed since the onset of stroke symptoms for use as an additional input data values for the patient assessment profile.

In some embodiments, the processor utilizes the patient's pre-morbid status, general health and co-morbidities as an additional input data values for the patient assessment profile.

In some embodiments, the processor utilizes the patient's advanced directives as an additional input data values for the patient assessment profile.

In some embodiments, the processor utilizes current medications and/or medical history of patient that significantly influence decision making as an additional input data values for the patient assessment profile, including blood thinners and recent surgery.

In some embodiments, the processor provides an imaging interface to connect to an imaging device to receive the brain scan image files, the imaging device selected from the group consisting of a scanner, a picture archiving communication system network, and a cloud image storage device.

In some embodiments, the processor determines the estimated transport time and the estimated treatment time comprises determining a required treatment for the patient and identifying one or more available treatment facilities based on available treatment services and equipment, available treatment times, available transportation type and the required treatment of the patient.

In some embodiments, the processor continuously updates the patient assessment profile using a feedback loop based on additional input data values including configurations for the current physician and health system, additional available patient and health system data, changes configurations for the physician and health care facility, updates the one or more weighting factors, and processes control commands received from a display device displaying the visual representation.

In some embodiments, the processor constructs and continuously validates the patient assessment profile and the input data values using current and future clinical trial datasets.

In some embodiments, the processor constructs and continuously validates the patient assessment profile by receiving additional data and results on adjuvant therapies including neuro-protection and augmented thrombolytic techniques to change physician and health system heuristics.

In some embodiments, the processor receives threshold data for a health care provider to update and customize the patient assessment profile, the weighting factors, and the input data values for the health care provider, the health care data including number of treatment centers providing endovascular treatment, staff availability, and other current health care metrics.

In some embodiments, the processor determines the patient assessment profile further comprises determining a rate of brain tissue death using collateral assessment on CTA, CT Perfusion, MRI or a combination of thereof.

In some embodiments, the processor determines the likelihood of the thrombus dissolving the over future time is determined by one or more techniques of measuring thrombus morphology such as a size of the thrombus, length of the thrombus, surface area of the thrombus, volume of the thrombus, and permeability to blood flow of the thrombus.

In some embodiments, the processor determines a likelihood of the thrombus dissolving with administration of a thrombolytic drug using the thrombus morphology and the collateral blood flow, the patient treatment protocol indicating the likelihood of the thrombus dissolving with administration of the thrombolytic drug.

In some embodiments, the processor determines the output data values of the patient assessment profile that indicates a comparison between risks of the administration of a thrombolytic drug and risks of endovascular treatment, the risks including a bleeding risk and other potentially major risks associated with thrombolytic drug administration and a treatment risk of not being able to administer the endovascular treatment or not successfully providing the endovascular treatment.

In some embodiments, the processor determines the collateral blood flow using mCTA, $T_0$ and $T_{max}$ values.

In some embodiments, the processor determines the patient brain electronic images of one or more imaging modalities selected from the group consisting of CT scan, multi-phase CTA, and CT perfusion, MRI, TCD, EIS and other imaging modalities.

In some embodiments, the processor determines the patient treatment protocol selected from the group consisting of: transferring the patient to the treatment facility for treatment with endovascular therapy; transferring the patient to the treatment facility for direct treatment without additional or repeating brain scans; retaining the patient at an initial treatment facility for treatment with a thrombolytic drug; and retaining the patient at the initial treatment facility.

In some embodiments, the processor is configured to: receive additional patient, clinical and imaging data for stroke patients; update the input data values using the additional patient, clinical and imaging data for stroke patients; and update patient treatment protocol using machine learning and the additional patient data, health system data, the updating by applying additional weighting factors to the updated input data values.

In some embodiments, the processor determines the treatment protocol as the visual representation on a time-based Computed Tomography Perfusion (CTP) map interface.

In some embodiments, the processor determines the treatment protocol indicates one or more of an automated prediction of thrombus lysability using the thrombus morphology, an automated quantitation of collateral status on a CTP map and on multi-phase CTA and an automated assessment of severe hypoattenuation on non-contrast CT.

In another aspect, there is provided an imaging system for evaluating a patient suffering from acute stroke. The imaging system receives patient brain electronic images. The imaging system has a decision support computing tool with a processor to: receive patient clinical information; generate a patient brain imaging profile using the patient brain scan electronic images and the patient clinical information, the imaging profile identifying a quantity and eloquence of brain tissue that is irreversibly infarcted, a rate or estimated quantity of patient brain tissue that likely will become irreversibly infarcted at a future time, a thrombus morphology associated with a likelihood of a thrombus dissolving at the future time, and an estimated collateral blood flow; determine an estimated transport time to transfer the patient to a treatment facility and an estimated treatment time for receiving reperfusion at the treatment facility; and dynamically determine a patient assessment profile by: processing the patient clinical information, the patient brain imaging profile, the estimated transport time, and the estimated treatment time to generate input data values; dynamically deriving weighting factors as an assessment of importance or relevance of the input data values and assigning the weighting factors to the input data values; deriving as output data values for the patient assessment profile using the input data values and the weighting factors, the output data values being a probability of an expert treatment decision for transferring the patient to the treatment facility and providing the reperfusion at the treatment facility, and a visual representation of the thrombus morphology, the estimated collateral blood flow, and an estimated quantity of brain tissue that will likely become irreversibly infarcted after the estimated transport time and/or the estimated treatment time using the rate or the estimated quantity of patient brain tissue that likely will become irreversibly infarcted at the future time. The imaging system has an output device to output the patient treatment protocol as clinical decision support information.

In some embodiments, the imaging system determines that the patient is already at the treatment facility and updating the visual representation with the estimated quantity of brain tissue that will likely become irreversibly infarcted after the estimated treatment time for receiving reperfusion.

In some embodiments, the imaging system determines a patient clinical data profile identifying an age or age range for the patient and a stroke severity, the stroke severity defined on a scale of mild, moderate and severe or based on physician heuristics, and determining the patient assessment profile using the patient clinical data profile as input to the system model.

In some embodiments, the imaging system determines the time elapsed since the onset of stroke symptoms as an additional input data value for the patient assessment profile.

In some embodiments, the imaging system determines the patient's pre-morbid status, general health and co-morbidities as additional input data values for the patient assessment profile.

In some embodiments, the imaging system determines the patient's advanced directives as an additional input data value for the patient assessment profile.

In some embodiments, the imaging system determines current medications and/or medical history of patient that significantly influence decision making as an additional input data values for the patient assessment profile, including blood thinners and recent surgery.

In some embodiments, the imaging system provides an imaging interface to connect to an imaging device to receive the brain scan image files, the imaging device selected from the group consisting of a scanner, a picture archiving communication system network, and a cloud image storage device.

In some embodiments, the imaging system determines the estimated transport time and the estimated treatment time comprises determining a required treatment for the patient and identifying one or more available treatment facilities based on available treatment services and equipment, available treatment times, available transportation type and the required treatment of the patient.

In some embodiments, the imaging system continuously updates the patient assessment profile using a feedback loop based on additional input data values including configurations for the current physician and health system, additional available patient and health system data, changing configurations for the physician and health care facility, updates for the one or more weighting factors, control commands received from a display device displaying the visual representation.

In some embodiments, the imaging system continuously validates the patient assessment profile and the input data values using current and future clinical trial datasets.

In some embodiments, the imaging system continuously validates the patient assessment profile by receiving additional data and results on adjuvant therapies including neuro-protection and augmented thrombolytic techniques to change physician and health system heuristics.

In some embodiments, the imaging system receives threshold data for a health care provider to update and customizes the patient assessment profile, the weighting factors, and the input data values for the health care provider, the health care data including number of treatment centers providing endovascular treatment, staff availability, and other current health care metrics.

In some embodiments, the imaging system continuously validates the patient assessment profile further comprises determining a rate of brain tissue death using collateral assessment on CTA, CT Perfusion, MRI, TCD, EIS, or a combination of thereof.

In some embodiments, the imaging system continuously validates the likelihood of the thrombus dissolving the over future time is determined by one or more techniques of measuring thrombus morphology such as a size of the thrombus, length of the thrombus, surface area of the thrombus, volume of the thrombus, and permeability to blood flow of the thrombus.

In some embodiments, the imaging system continuously validates a likelihood of the thrombus dissolving with administration of a thrombolytic drug using the thrombus morphology and the collateral blood flow, the patient treatment protocol indicating the likelihood of the thrombus dissolving with administration of the thrombolytic drug.

In some embodiments, the imaging system continuously validates the output data values of the patient assessment profile that indicates a comparison between risks of the administration of a thrombolytic drug and risks of endovascular treatment, the risks including a bleeding risk and other potentially major risks associated with thrombolytic drug administration and a treatment risk of not being able to administer the endovascular treatment or not successfully providing the endovascular treatment.

In some embodiments, the imaging system determines the collateral blood flow is using mCTA, $T_0$ and $T_{max}$ values.

In some embodiments, the imaging system determines the patient brain electronic images using one or more imaging modalities selected from the group consisting of CT scan, multi-phase CTA, and CT perfusion, MRI, TCD, US, EIS and other imaging modalities.

In some embodiments, the imaging system determines the patient treatment protocol as selected from the group consisting of: transferring the patient to the treatment facility for treatment with endovascular therapy; transferring the patient to the treatment facility for direct treatment without additional or repeating brain scans; retaining the patient at an initial treatment facility for treatment with a thrombolytic drug; and retaining the patient at the initial treatment facility.

In some embodiments, the imaging system is configured to: receive additional patient, clinical and imaging data for stroke patients; update the input data values using the additional patient, clinical and imaging data for stroke patients; and update patient treatment protocol using machine learning and the additional patient data, health system data, the updating by applying additional weighting factors to the updated input data values.

In some embodiments, the imaging system determines the treatment protocol as the visual representation on time-based a Computed Tomography Perfusion (CTP) map interface.

In some embodiments, the imaging system determines the treatment protocol as one or more of an automated prediction of thrombus lysability using the thrombus morphology, an automated quantitation of collateral status on a CTP map and on multi-phase CTA and an automated assessment of severe hypoattenuation on non-contrast CT.

BRIEF DESCRIPTION OF THE DRAWINGS

In the figures, embodiments are illustrated by way of example. It is to be expressly understood that the description and figures are only for the purpose of illustration and as an aid to understanding.

Embodiments will now be described, by way of example only, with reference to the attached figures, wherein:

FIG. 5 is a table for an example of a multivariable logistics regression model that uses constructs in FIG. 4 to determine thrombus dissolution rates.

DETAILED DESCRIPTION

Embodiments described herein may provide methods, systems, and apparatus for triaging decision support tools that can assist in the decision-making at a hospital or other health care facility for treatment of stroke patients, such as for example, whether or not to implement endovascular therapy, transfer the patient to a facility capable of endovascular therapy, administer thrombolytic drugs, or perform additional imaging.

Figure 1:
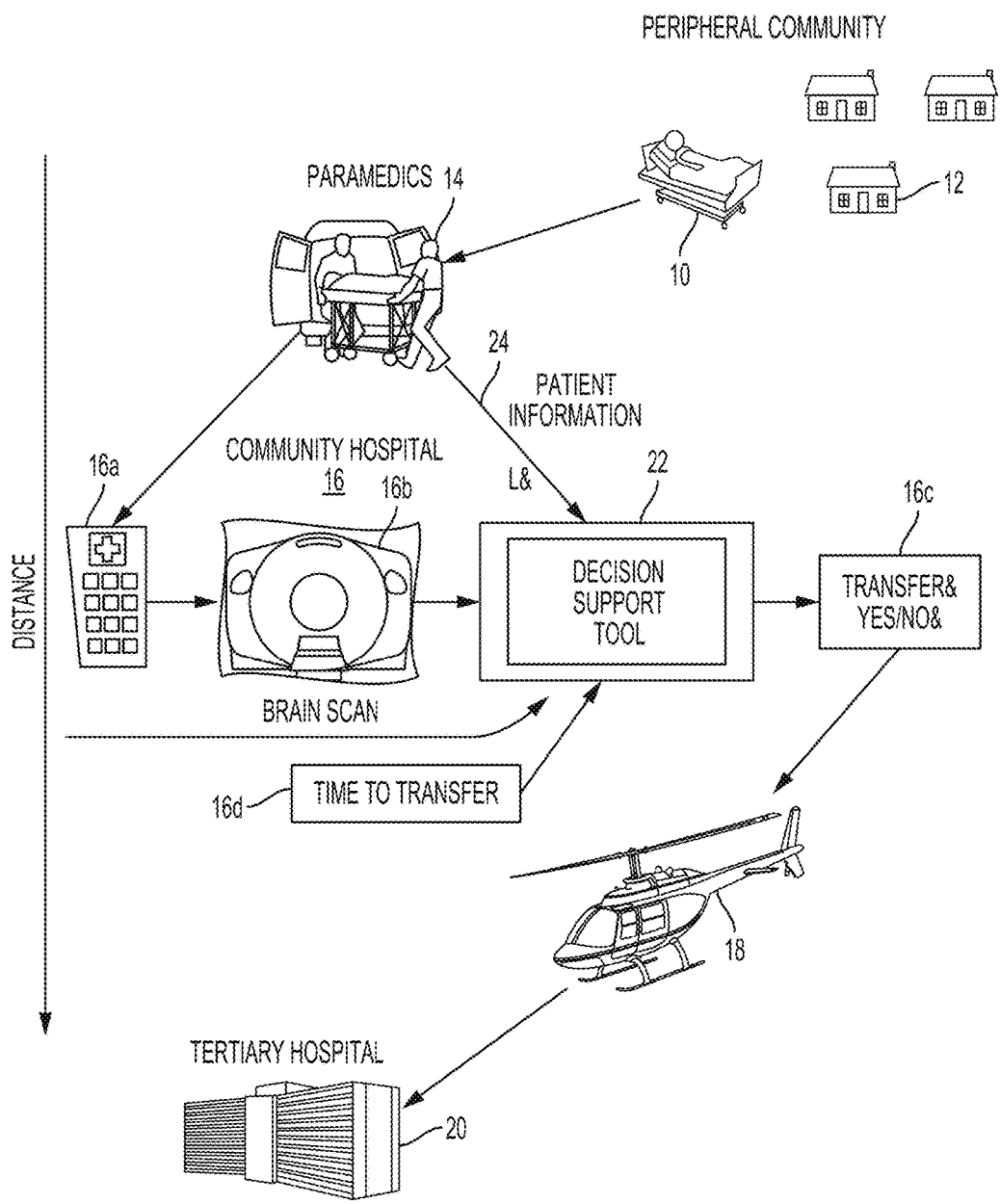
FIG. 1 is a schematic diagram showing a triaging tool and interaction of a patient and medical facilities according to some embodiments.

FIG. 1 is a schematic diagram of the triaging process from home to community hospital to the tertiary hospital in a hub and spoke stroke care model as an illustrative example embodiment. The triaging decision support tool 22 may make the process more efficient.

As shown in FIG. 1, a patient 10 in a peripheral community 12 may be suffering a stroke and transferred by paramedics 14 to an emergency room 16a of a community hospital 16. At the community hospital 16, a scanner or imaging device may generate one or more brain and neurovascular brain scan electronic images 16b (in a variety of imaging modalities) to provide electronic data to a computer device or decision support tool 22 that seeks to automatically answer the question 16c whether the patient should be transferred using a transportation vehicle 18 (of various types) to a tertiary hospital 20 and time to transfer 16d. The tool 22 may implement machine learning techniques based on expert physician data, clinical data, imaging data, and so on. Other automated answers may also be provided as described herein. For this illustrative example, the decision support tool 22 receives brain scan electronic images 16b as input from an imaging device, estimated time data (e.g. time to transfer to facility 16d, time for treatment), patient clinical information 24, and other input data.

The decision support tool 22 may be configured to provide an automated tool that takes into account various imaging and clinical factors captured as input data sources in providing information to assist a physician in determining the answer to the question "Should this stroke patient be sent to the hospital where endovascular therapy is available right now?". The decision support tool 22 (which may be referred to herein as the tool for simplicity) may be updated and refined using heuristic and machine learning techniques. The tool 22 may implement mathematical and statistical models for aspects of embodiments described herein. The tool 22 may also provide an expeditious and appropriate automated answer or other decision support information for a healthcare provider. The possible automated answers may include:

Transfer the patient as soon as possible to the tertiary hospital for treatment with endovascular therapy. This may also involve a treatment with thrombolytic drugs despite a low (but non-zero) likelihood of successful recanalization of the occluded vessel with this therapy.

Transfer the patient as soon as possible to the tertiary hospital for endovascular therapy but do not treat the patient with the thrombolytic drug given futility and increased harm with the latter.

Do not transfer the patient. Keep the patient at the primary hospital and treat him/her with thrombolytic drugs only as there is a high likelihood of successful recanalization of the occluded vessel with this therapy.

Do not transfer the patient because a large or critical volume of the brain is already irreversibly damaged or will die before the patient could be transferred and undergo successful treatment at the tertiary hospital.

Do not transfer the patient. Keep the patient at the primary hospital and treat him/her with thrombolytic drug only because the patient is not eligible for endovascular treatment for reasons of pre-morbid medical conditions, arterial anatomy or other medical reasons.

Various example factors that are input into the tool 22 and system model may be divided into example categories: 1) clinical factors, 2) imaging factors, 3) estimated time required to transfer the patient to the tertiary hospital (or other care facility), and 4) estimated time to receive treatment.

Figure 2:
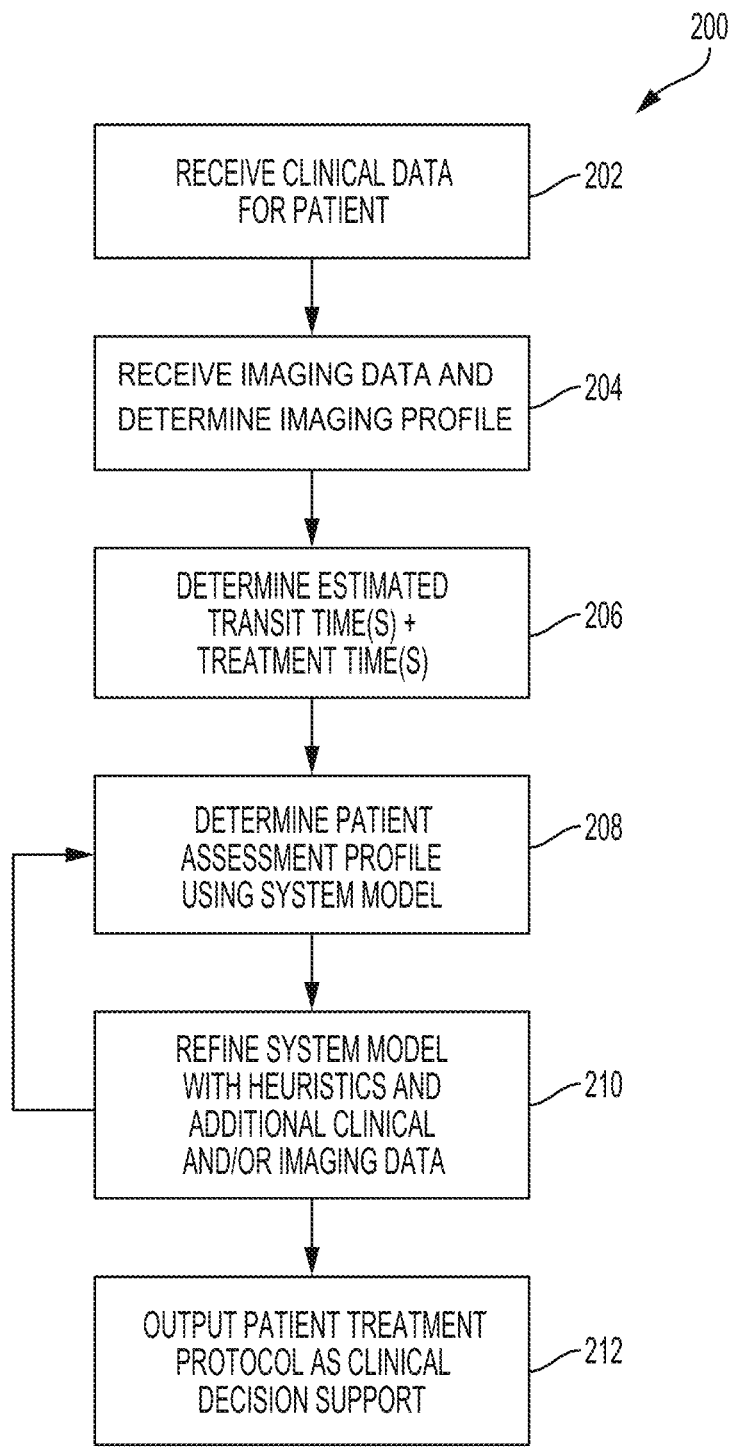
FIG. 2 is a flow chart diagram of a process for an automated triaging decision support tool according to some embodiments.

FIG. 2 is a flow chart diagram of an illustrative process for an automated triaging decision support tool according to some embodiments.

Input Information—Clinical Factors

At 202, the tool 22 receives clinical data for a patient. The tool 22 may also receive clinical data for other patients to help construct and validate the statistical and mathematical model configuration as will be described herein. The tool 22 may complete missing data points using estimate and computed means for example. As additional input data becomes available the tool 22 may adjust to the additional input data and provide updated output results.

Illustrative example clinical factors that may input into the tool 22 include:

The age of the patient.
Severity of the patient's clinical situation.
Duration of the patient's symptoms.
The patient's pre-stroke functional status.

Patient's advance directives and expectations regarding quality of life

Further information regarding a computer application that can provide directives and patients' expectations is provided, for example, in International Patent Application Serial No. PCT/CA2014/050899 entitled Systems and Methods for Obtaining and Displaying Medical Data to Assist Decision Making During a Medical Emergency the entire contents of which is hereby incorporated by reference.

The age of the patient may be determined or estimated when a patient arrives at the hospital. The patient data may be part of a hospital information system (HIS) or a radiology information system (RIS) and integrated with or accessed by the tool 22. Nursing personnel or physicians may collect primary information on the stroke severity using a simple standardized scale, such as mild, moderate or severe. The scale may also be a scale of values or factors. The severity scale may take into account the patient's comprehension, level of consciousness, speech and motor function of face, arm and leg, for example. This may be done using the NIH stroke scale as another example.

The duration of the patient's symptoms is input in minutes based on the information available to the nursing personnel or physicians from witnesses and/or emergency response personnel. In some cases, a precise time of onset of stroke symptoms is not known. In such cases, the last seen normal time may be provided as input.

The patient's pre-stroke functional status may be determined using a questionnaire that takes into account the patient's capabilities prior to the current event, such as the Barthel Index which records the capacity to perform activities of daily living. In some cases, this information is not available due to the emergency nature of the patient's condition. In such cases, that information is inputted as "unknown" and the system model may adapt accordingly.

The patient's pre-stroke advanced directives may be determined by the treatment medical team (physicians, nurses), may be available on-line as part of a health record system or a patient database. In some cases, this information is not available due to the emergency nature of the patient's condition. In such cases, that information is inputted as "unknown" and the system model may implement machine learning to adapt accordingly.

There may be a variety of reasons why the initial patient clinical data set is incomplete. For example, a patient may not conscious, no family around, patient is not cooperative, patient cannot be given IV contrast: e.g. contrast allergy, poor kidney function, imaging attempted but of poor quality due to patient motion, institutional policy (e.g. do not do CT perfusion), equipment issues (too old, some things cannot be done, equipment failed halfway through the procedure) and so on. Another factor may be the condition of the patient, such as a fluctuating patient and improving patient.

At 204, the tool 22 receives imaging data for a patient including the electronic images from the patient brain scan.

Input Information—Imaging Factors

Several inputs in the tool 22 may be based on the electronic images or scans produced from various brain scan or imaging devices. The imaging may be conducted when the patient arrives at the hospital, for example. Different imaging modalities, technologies and formats may be used, as described herein. Different imaging technologies may also provide meta-data about the patient in addition to electronic images.

For example, electronic images may be generated from a CT scan of the patient's brain to rule out a hemorrhagic stroke (i.e. a bleed) prior to proceeding with additional CT scans to determine if the stroke is an ischemic stroke. The image set may be updated over time. The physician may also use magnetic resonance (MR) brain imaging modality, or another brain and neurovascular imaging device. The tool 22 may work with both CT and MR, for example. Further examples of other imaging techniques that the tool 22 may work with include electrical impedance spectroscopy for imaging brain to provide realistic non-invasive assessments of the brain including occluded arteries. TCD is also another example technique.

The tool 22 may automatically process the images to generate a patient brain imaging profile. The imaging profile may include the images, and additional meta-data identifying a quantity and eloquence of brain tissue that is irreversibly infarcted, a rate or estimated quantity of patient brain tissue that likely will become irreversibly infarcted at a future time, a thrombus morphology associated with a likelihood of a thrombus dissolving at the future time, and an estimated collateral blood flow.

Further example imaging factors include:
  The amount and location of brain tissue that is already irreversibly damaged and the amount and location of brain tissue that will likely die before the time the patient reaches the tertiary hospital from the community hospital and could undergo successful treatment.
  Presence of a target thrombus causing a proximal intracranial occlusion.
  The likelihood of the thrombus in the patient's head dissolving quickly and blood flow be adequately restored (reperfusion) with the administration of the thrombolytic drug.
  The risk of giving the thrombolytic drug compared to the risks of endovascular treatment.
  The likelihood of success of endovascular treatment in restoring blood flow (reperfusion) based on access factors e.g. severe tortuosity.

Determination of the Amount of Irreversibly Infarcted Brain Tissue and the Amount that Will Likely Die In some embodiments, the tool 22 uses techniques to automatically determine the amount of brain tissue that is likely irreversibly infarcted at the time of initial brain scan. The tool 22 uses techniques to also automatically determine the amount of brain that will likely die in the time it takes for the patient to be transferred from the community hospital to the endovascular capable hospital. This automated image processing may use different types of brain scans and imaging modalities to determine metrics of the imaging profile such as a non-contrast CT scan; multi-phase CTA; CT Perfusion or MRI, MR Perfusion, and MR angiography. Example metrics are described herein such as the amount of brain tissue irreversibly infarcted at time of scan and estimated to be irreversibly infarcted after transfer to endovascular capable hospital.

The tool 22 is capable of deriving triaging decisions from each of these scans individually but can use other scans if and when available to increase accuracy around the triaging decisions and provide more nuanced information. The tool 22 is flexible which is relevant from an acute stroke treatment perspective. Sometimes, the patient's clinical situation is such that a multi-phase CTA or CT perfusion is not available because the patient is allergic to the contrast dye used in these scans or the patient has kidney disease. The tool 22 may use the non-contrast CT data to make the triaging decision. Other times, the patient moves on the scanner or is agitated, thus resulting in only one type of scan available, the other scans being of poor quality due to patient motion. The tool 22 may identify poor quality images and use the available information from the best scan to make a triaging decision. Some hospitals, due to logistics or physician preferences, may only use one or two types of scans. The tool 22 is flexible enough to provide relevant triaging information using the scans the hospitals has access to.

In some embodiments herein, the tool 22 may use non-contrast CT scan images which is a brain scan image available in most treatment facilities or hospitals with CT scanners. A non-contrast CT scan image may be used to determine the amount of brain tissue that is already irreversibly infarcted. As an example, the extent and volume of brain tissue that is likely already irreversibly infarcted may be delineated using an intensity-based region-growing algorithm that assesses all neighboring regions of a segmented brain volume to determine if those regions should be included or not. The regions may be provided as part of the visual representation for display on a display device. If the centers use MR imaging, the tool 22 may use diffusion imaging to determine the amount of brain tissue that is irreversibly infarcted and a GRE (Gradient Recalled Echo) or SWI (susceptibility weighted imaging) sequence may be used to rule out bleeding risk.

Transfer may be futile if a large volume of brain at risk is already irreversibly infarcted. In some embodiments herein, the tool 22 takes into account the possibility that one or two of the three possible brain scans (i.e. non contrast CT, multi-phase CTA or CT Perfusion) will either be unavailable or be of insufficient quality to be used. For example, a brain scan may not be used if a patient has moved during the scan or there is poor contrast on the images, the resulting determination would be discarded or given a lesser weighting in the final determination.

In some embodiments, for example, a single or preferably multi-phase CTA may be used to automatically determine collateral status. Collaterals are backfilling pial vessels beyond a thrombus seen on brain scans. Patients with good collaterals may have a brain that may be saved by removing the thrombus while patients with poor collaterals may not have any brain worth saving in some circumstances. In case of multi-phase CTA datasets, a temporal maximum intensity projection may be used to generate a single CTA dataset, which is independent of the acquisition time. An advanced vessel segmentation framework may be employed to automatically extract the vessels from this CTA dataset. After this, the two hemispheres may be automatically separated, e.g. by non-linear registration of a brain atlas to the NCCT dataset. After separation of the hemispheres, the volume of the segmented vessels may be calculated for the affected and unaffected hemisphere. In doing so, a ratio between the vessel volume in the affected and the vessel volume in the unaffected hemisphere may be calculated. Here, it is assumed that values close to one indicate a good collateral situation while lower values indicate a poor collateral situation. This information, which becomes available in 4-8 pre-specified brain regions, by calculating this ratio for each phase of the multi-phase CTA dataset, will determine collateral status and therefore the amount of brain that is already irreversibly infarcted. The automatically determined collateral score (ratio of the vessel volumes in the affected and unaffected hemisphere) on the mCTA datasets will be validated by comparison to determine pial arterial filling score using Spearman's correlation to help improve accuracy of the automatic determinations.

Information on collateral status in each brain region may also aid in determining if that brain region will be irreversibly infarcted in the time it takes to transfer the patient to the endovascular capable care facility. Brain regions with intermediate collaterals may only survive if the thrombus blocking blood supply to that part of the brain is removed quickly. Arrival at the tertiary hospital may need to be less than a specific time threshold away (e.g. estimate 180 minutes) due to transport distance and availability of treatment modality for the treatment to be effective. For example, a brain with intermediate collaterals may only survive for an estimated time period and the time for transfer and treatment should be less than that time to be effective. Only a brain with good collaterals may be likely to survive if the tertiary hospital is more than the specific time threshold (e.g. 180 minutes) away. Automated regional assessment of collateral status using the tool 22 may help physicians making this determination. Collateral assessment may also be determined from the source images of CTP. In a facility or centre using MR imaging, an MR angiogram may be used to determine the site of occlusion and collateral status using a similar technique as outlined above for CT scans.

In some embodiments, an image scan called CT Perfusion or CTP may be used. This scan calculates blood flow in the brain. The tool 22 is configured with automated software (e.g. as used and refined at steps 208 and 210 of FIG. 2) that determines a probability of the amount of brain that is likely to be irreversibly infarcted even if the thrombus is removed very early and the probability of brain that is alive now but not likely to remain alive over the time it takes to transfer or transport the patient to the endovascular capable hospital. To do so, a cerebral blood flow (CBF) map and a time-to-maximum ($T_{max}$) map of the impulse residue function (IRF) may be automatically generated by tool 22 using techniques described herein. $T_{max}$ is defined as the sum of the time ($T_0$) of the first non-zero value of the IRF plus one-half the area underneath the IRF (or mean transport time, MTT), in some illustrative examples.

Figure 7:
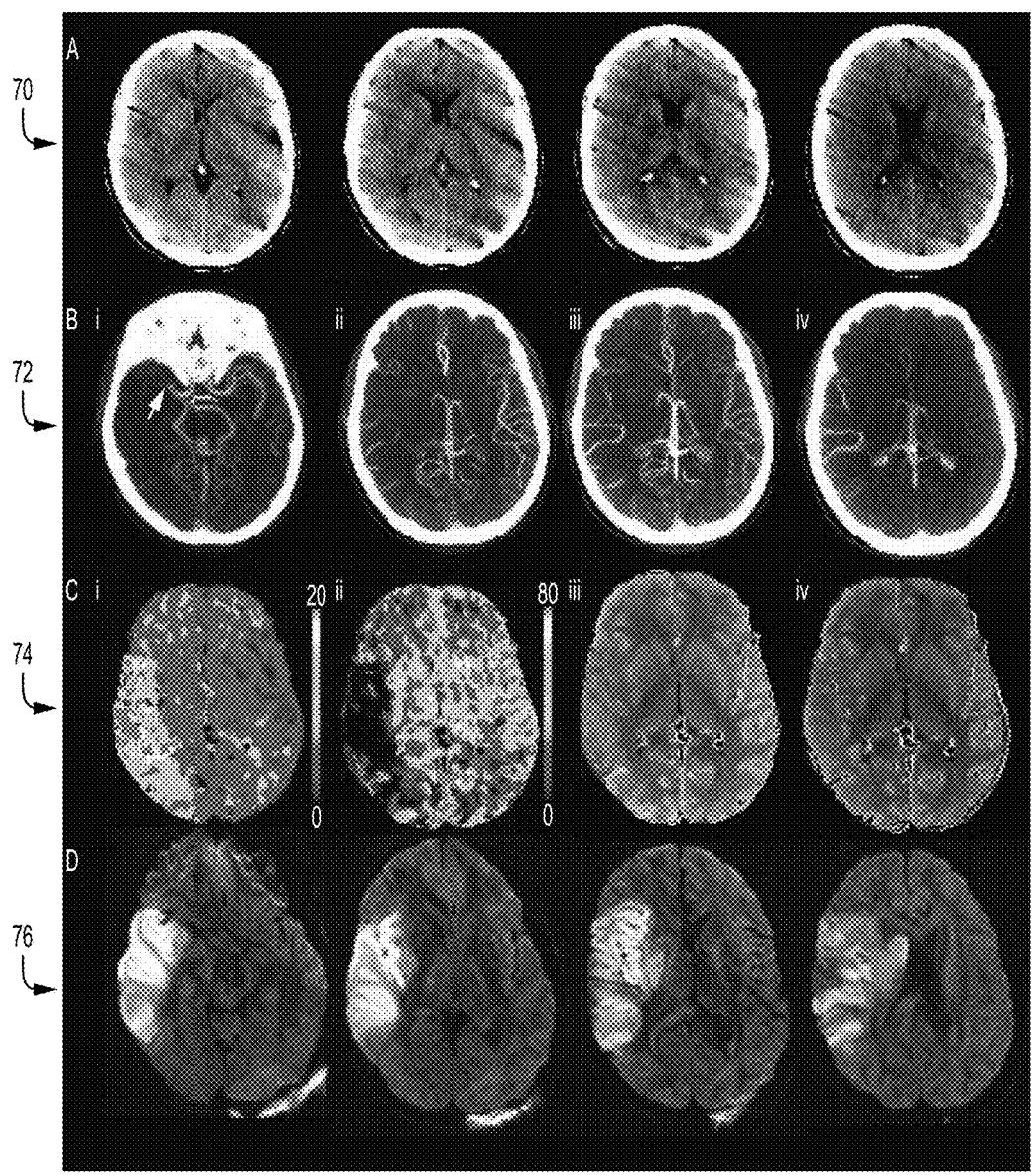
FIG. 7 is a screenshot of visual representations of image slices from multi-modal imaging including non-contrast CT, multi-phase CTA and CT Perfusion. The bottom panel shows final infarct. The tool may use any or all of these imaging modalities to estimate infarct over time.
Figure 8:
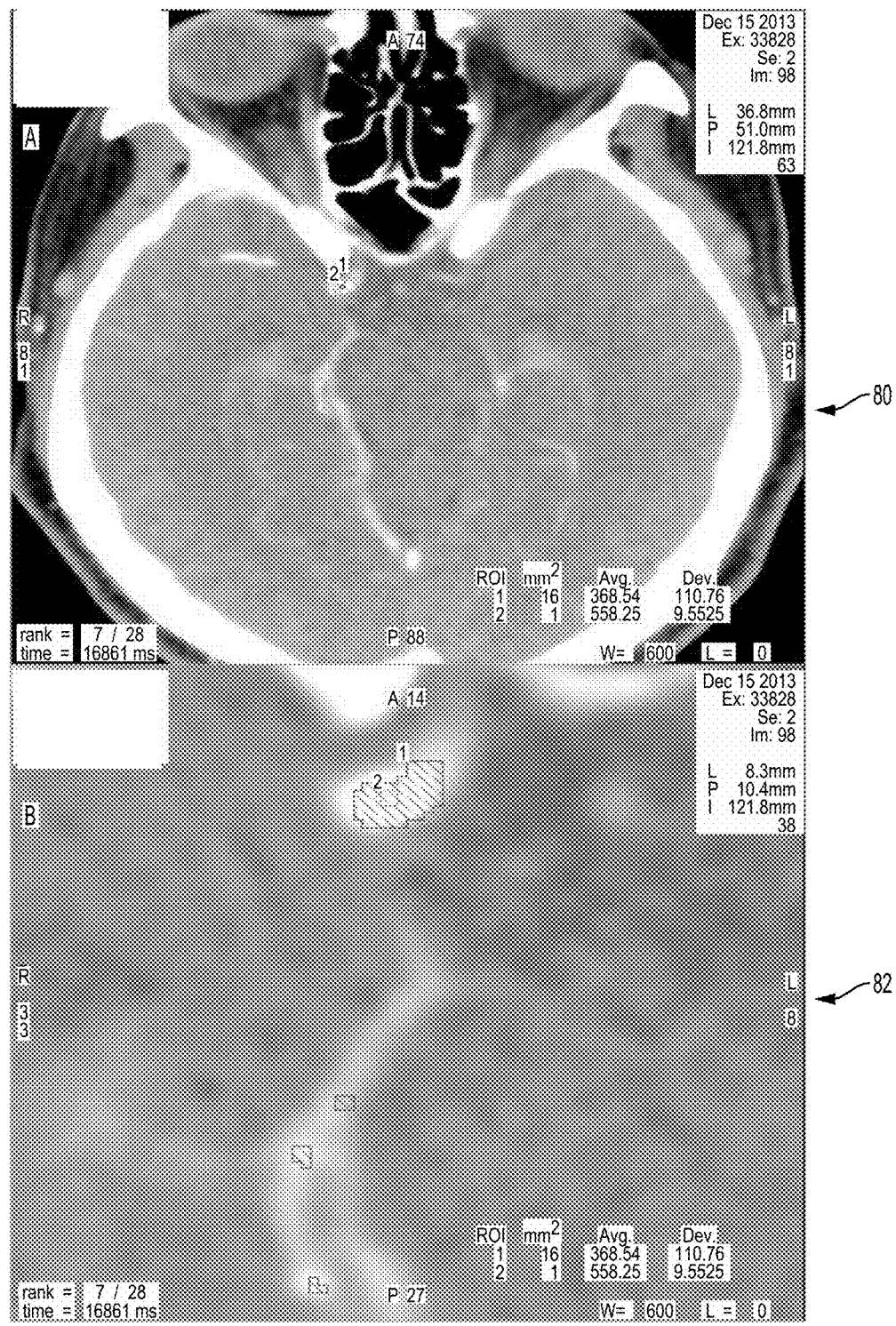
FIG. 8 is a screenshot of visual representations of image slices for from automatic generation of arterial input function for use in CT Perfusion.
Figure 11:
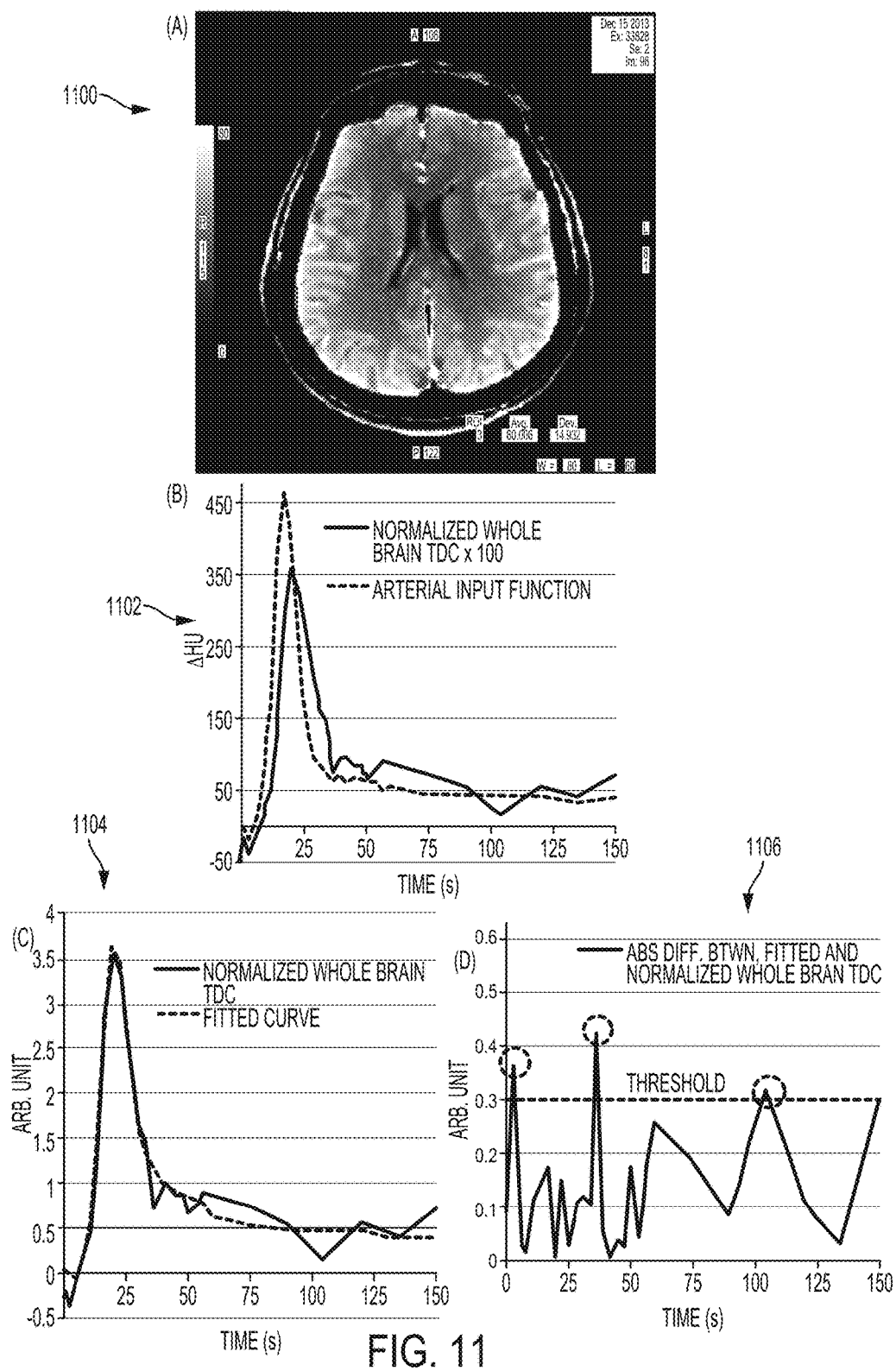
FIG. 11 is a screen shot of a visual representation of an image slice of a CTP study according to some embodiments that demonstrates techniques for patient motion correction.
Figure 12:
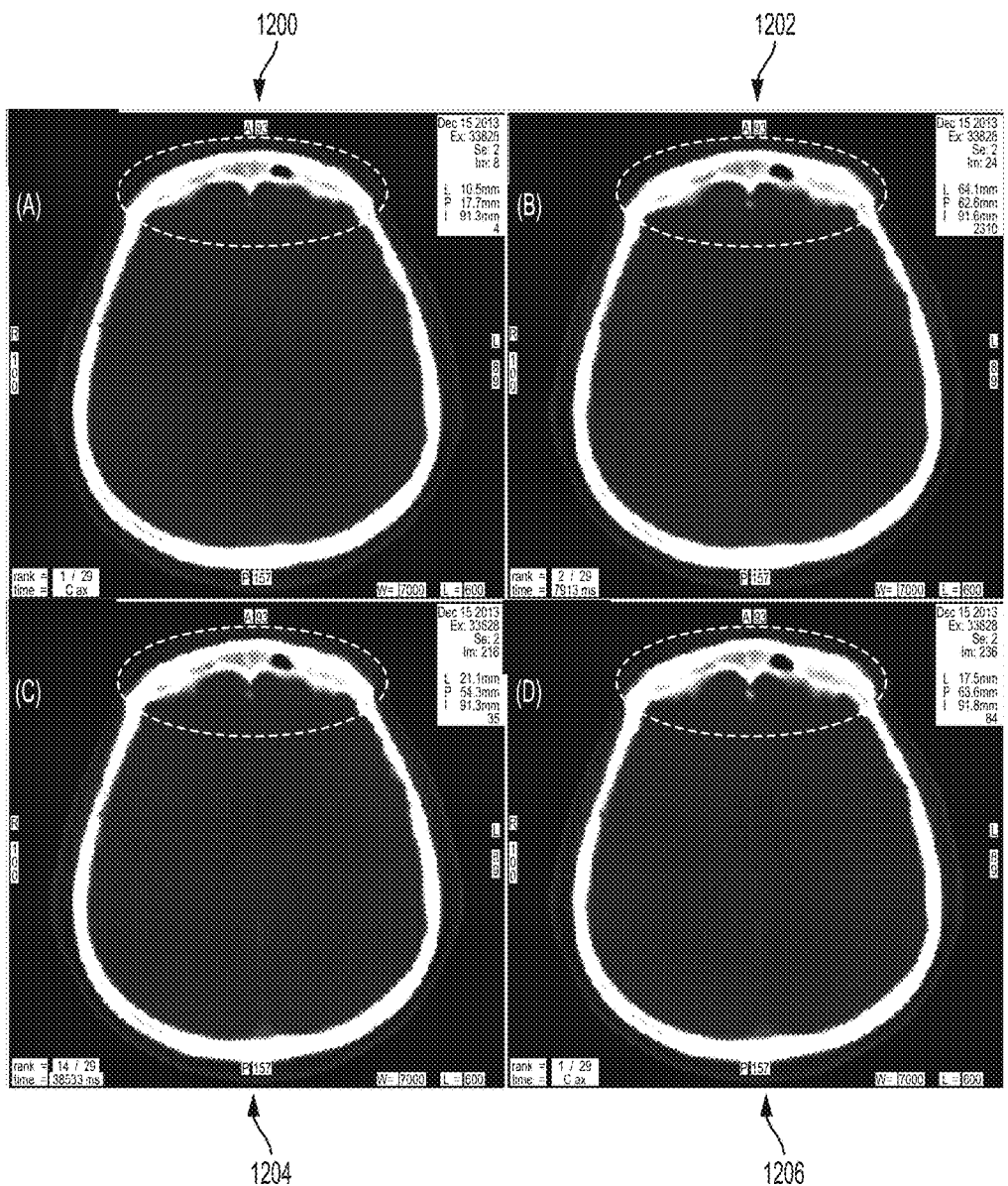
FIG. 12 is a screen shot of a visual representation of image slices of a CTP study that shows patient (e.g. head) motion in the Z-axis.
Figure 13:
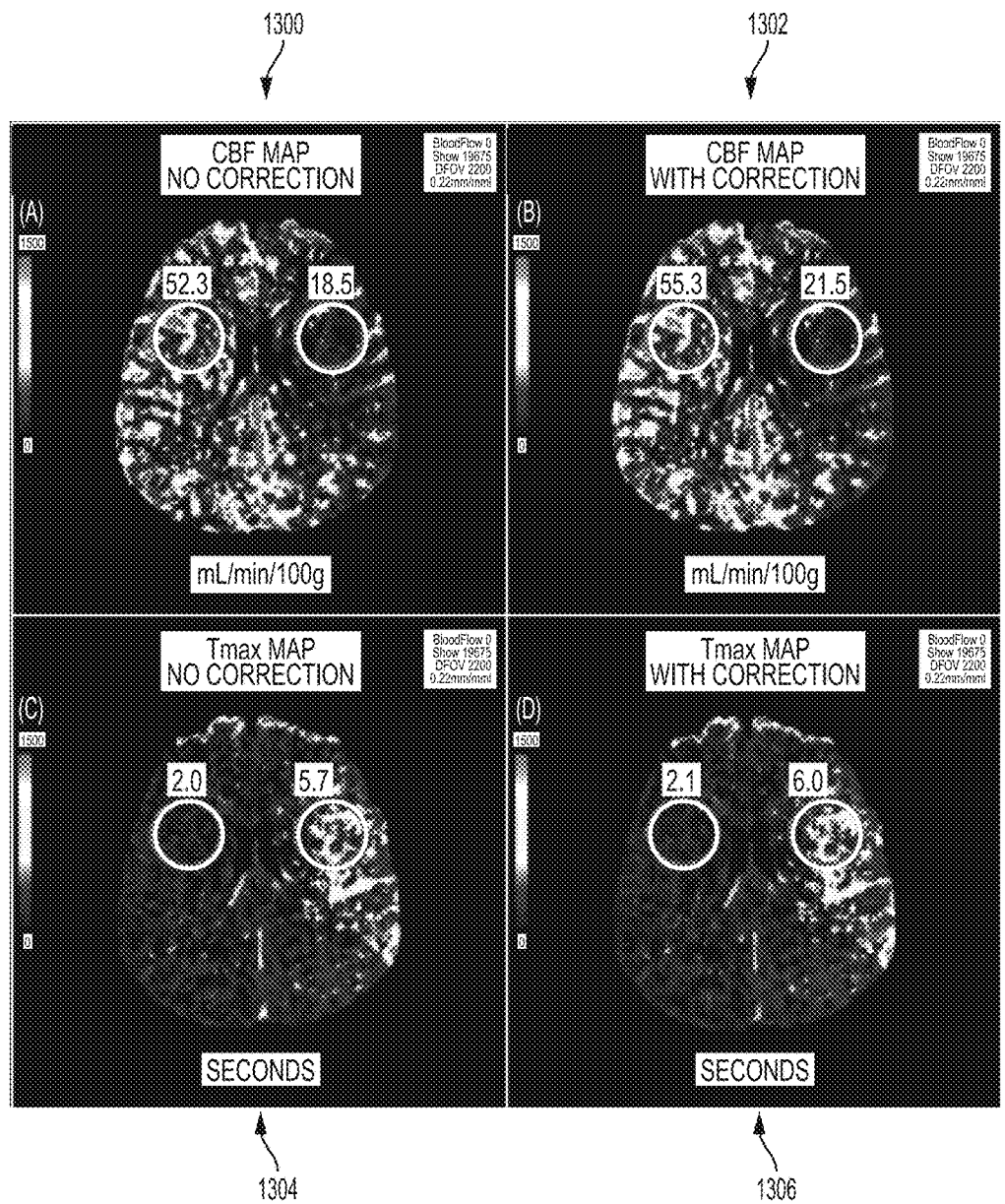
FIG. 13 is a screen shot of a visual representation of image slices of a CTP study showing the effect of z-axis motion on perfusion parameter maps of a CT Perfusion Study. The CBF and Tmax maps with and without z-axis motion correction are shown together with the mean value within a circular region of interest within the stroke affected hemisphere and contralateral hemisphere.
Figure 14:
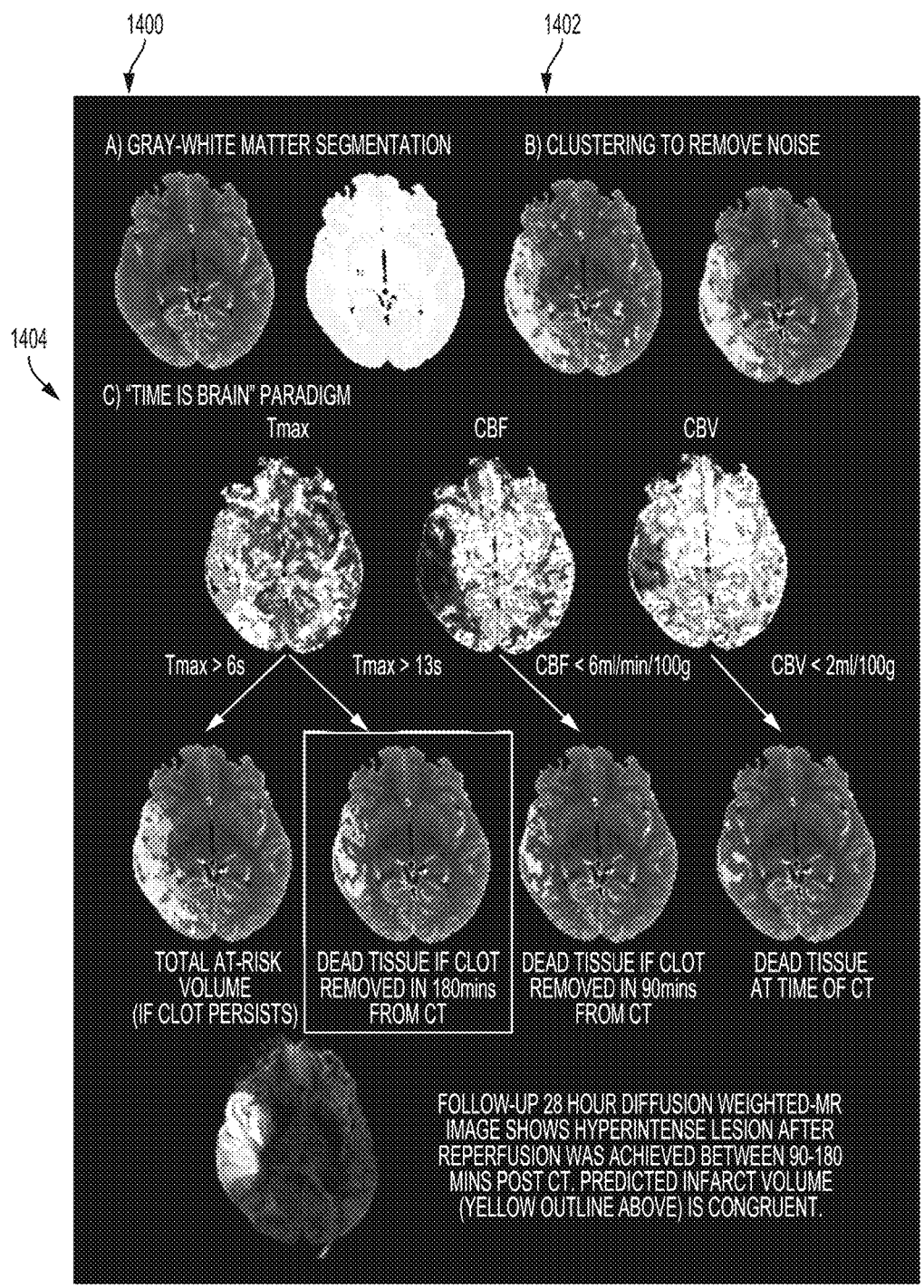
FIG. 14 is a screen shot of visual representations of image slices from an application of time-based infarct growth according to some embodiments.

In some embodiments, the tool 22 may use CT Perfusion studies (e.g. images) that include the intracranial internal carotid or basilar arteries in the field of view. The z-axis (axial) coverage of a CT Perfusion study may be limited to 4-8 cm on many CT scanners available to community hospitals. 3D registration to account for axial motion may not be optimal as it could lead to loss of entire slices for calculation of hemodynamic maps. Instead, the tool 22 may use 2D rigid registration to remove in-plane motion in CTP studies. After 2D registration, there may be two automation tasks: to generate the arterial input function (AIF) and to remove motion in the z-axis for each slice. For the AIF task, the tool 22 may first remove bone and air voxels from all slices by thresholding the first image. The tool 22 may background subtract the time-density curve (TDC) of each remaining voxel by subtracting the baseline value before contrast arrives from all data points. TDCs with an area under the curve (AUC) larger than 95% of the maximum AUC of all TDCs are then classified into two groups by K-means classifier corresponding to arteries and veins. As the mean TDC from the artery group may have a steeper rising slope than that of the vein group, this feature can be used to separate the artery from the vein group of voxels (FIG. 8 image 80). For each slice, the TDC from four connected voxels with the highest AUC from the artery group will be chosen (FIG. 8 image 82). The slice TDC with the highest AUC among all slices may be taken as the AIF. For the removal of z-axis motion of each slice, a region-of-interest (ROI) will be automatically generated around the entire brain after removal of the skull from the AIF task (FIG. 11 image 1100). The TDC from this ROI may be baseline subtracted and normalized by the average value before it is fitted by deconvolution with the AIF from the first task (FIG. 11 image 1102 and image 1104). The absolute deviations of the fitted and the measured TDC at all time points will be determined (FIG. 11 image 1106). Images at time points where the deviations are more than 0.3 will be removed from the calculation of hemodynamic maps for this slice (FIG. 12 image 1206 and FIG. 13). Using the determined AIF, the tool 22 configured with CTP perfusion software may then calculate the following functional maps: cerebral blood flow (CBF) and $T_{max}$, cerebral blood volume (CBV), and MTT. As shown in FIG. 13, z-axis motion affects cerebral blood flow (CBF) and $T_{max}$ values determined by the tool 22 configured with CT Perfusion software. Since infarct growth may be determined using CBF and $T_{max}$ thresholds, it may be important to correct for z-axis motion Once the above step is accomplished, the tool 22 may use CTP-Average maps (e.g. averages of all images of the same slice in a CTP study) to create tissue segmentation masks (e.g. grey and white matter masks) by removing any cerebral spinal fluid or old infarcts as an example aspect of a visual representation. The tool 22 may separate gray matter (GM) and white matter (WM) based on pre-determined Hounsfield Unit thresholds (FIGS. 7 and 14). To remove any voxels caused by inherent noise, the system model will use a clustering method that will remove any single voxel that is not part of the confluent tissue of interest (FIG. 14 at 1402). The tool 22 may then superimpose these segmentation masks onto perfusion parameter maps created in step above (CBF, CBV, $T_{max}$ and MTT maps) (FIG. 14 at 1404). The system model will then use GM and WM time-dependent perfusion parameter thresholds that have already determined. Further examples are provided in Time-Dependent Computed Tomographic Perfusion Thresholds for Patients With Acute Ischemic Stroke by Bijoy Menon et al., the contents of which is hereby incorporated by reference. The tissue segmentation masks to predict current infarct volumes and infarct volumes at different times after successful reperfusion with IAT are arrived at as described herewith. The tool 22 will use a "double threshold" technique by first applying a $T_{max}$ threshold to define "total at-risk" tissue ($T_{max}$>6 seconds) and then sequentially applying the time dependent perfusion parameter thresholds shown as visual representations in FIGS. 9 and 10 for example, and shown in a patient in FIG. 14. These time-dependent perfusion parameter thresholds may also be validated using CTP and correlative imaging and clinical data from different trial databases.

Validation may involve using the CT Perfusion datasets acquired at baseline to generate perfusion parameter (PP) maps after motion correction as described herein. After this, the derived time-dependent thresholds derived by tool 22 may be applied to the PP maps to determine the expected final infarction at different follow-up times. Available timed follow-up imaging (NCCT or MR-DWI images) will be non-rigidly co-registered to baseline PP maps. Multiple neuro-radiologists (experts), blinded to the results of the PP maps, may delineate by consensus follow-up infarct regions of interest (ROIs) on the co-registered MR-DWI or NCCT images while excluding any small vessel disease abnormality or chronic/old infarct. The delineated follow-up infarction volumes may be compared to that derived from PP maps with the time-dependent thresholds using the Dice coefficient and the Hausdorff metric.

This validated probabilistic map of the dead or irreversibly infarcted brain tissue at different times following baseline brain scan may be correlated with the time information for transporting the patient to the tertiary hospital, the time required for treating the patient with the endovascular procedure and the likelihood of the patient's thrombus dissolving within that time will be used to determine the amount of tissue that will likely die within that time. A final map is then made showing the likely area of irreversibly infarcted brain at the time of the endovascular procedure. Further details regarding refinement, construction and validation of the system model with be provided herein in relation to FIG. 2 at 208, 210 and FIG. 22.

In some embodiments herein, the use of US imaging, TCD imaging, EIS imaging or other scanning technology may be used to identify the location of arterial occlusion and the likelihood of thrombus dissolution. This location will be used to determine the target for possible endovascular therapy.

In some embodiments herein, the physician at the community hospital may use visual information from the automated perfusion parameter maps or other scanning images as decision support in determining whether to transfer the patient to another treatment facility. That is, acceptable thresholds for tissue death overtime using all types of available brain scans are determined using statistical formulae based on pre-existing datasets and derived using assessments by expert physicians. For example, acceptable thresholds are determined for tissue that will likely die within 60 minutes, 120 minutes, 180 minutes, 240 minutes, and so forth.

In other example embodiments, for example in the context of fully automated systems, various thresholds for tissue death are used for each available brain scan, along with clinical information, information on geographic distance between community hospital and tertiary hospital, transport times and other inputs, to automatically determine whether the patient would have been transferred if an expert physician were making the decision. Details of this process are described further herein.

In other example embodiments, for example in the context of fully automated systems, various thresholds for tissue death are used for each available brain scan, along with clinical information, information on geographic distance between community hospital and tertiary hospital, transport times and other inputs, to automatically determine if the patient can directly be taken to the tertiary hospital's endovascular operating suite without doing repeat imaging at that center, thus saving costs of repeat imaging. Details of this process are described further herein.

In other embodiments, in centres using MR imaging an MR angiography or MR perfusion scan could be used to produce similar results. Similarly, combinations of different imaging modalities (CT, MR, TCD, US and EIS or other imaging type), depending upon availability could be used to produce output decision support results.

The Likelihood that the Thrombus Will Dissolve Early with the Thrombolytic Drug

Different example techniques may be integrated into the tool 22 to determine the likelihood of the thrombus dissolving early with the thrombolytic drug. These techniques use information on the size of the thrombus which may be defined by thrombus length, and using permeability and collateral blood flow.

Thrombus Length

The length of the thrombus in the patient's brain artery may be determined by tool 22 using multi-modal CT imaging. The non-contrast CT may be used to simply measure the hyperdense tubular middle cerebral artery on think axial (or other angle such as coronal or sagital) images through the circle of Willis. The tool 22 may use CT (NCCT), multiphase CTA and/or CTP, for example. The tool 22 may use one or all of the multimodal CT modality depending upon availability and image quality. In some example embodiments, the length of the thrombus in the patient's brain may be determined by tool 22 using a non-contrast CT scan. In other example embodiments, the tool 22 may use non-contrast CT (NCCT) and multi-phase CTA and/or CTP, varying by availability and scan quality, for this purpose. The tool 22 can use the CT perfusion and multi-phase CTA to improve accuracy of clot length determination on non-contrast CT. Note, the tool 22 may use CT Perfusion to determine clot permeability, or other imaging modalities in other example embodiments.

In case of multi-phase CTA, a temporal maximum intensity projection may be used to generate a single CTA dataset. After co-registration with NCCT, the bone tissue may be segmented in the NCCT dataset using Hounsfield value thresholds for bone tissue, for example. An advanced vessel segmentation framework may be employed to automatically extract the vessels from this CTA dataset. Using the 3D centerline representation of this vessel segmentation, all vessel endpoints that represent candidates for the proximal and distal ends of the thrombus will be identified. The 3D course of the vessel potentially occluded by a thrombus may be approximated for each vessel endpoint using the neighboring centerline voxels directly connected to the vessel endpoint. This allows expanding the centerline locally in the direction of the potential thrombus. This expanded centerline section may be used for a regional analysis of the Hounsfield values in the CTA and NCCT dataset along the expanded vessel, wherein it is assumed that a thrombus is represented in the resulting intensity profile by an increase of the Hounsfield values in the NCCT dataset and decrease of the Hounsfield values in the CTA dataset.

The tool 22 may also use patient specific Hounsfield values determined from the patient's non-contrast CT scan and an automatic 3D volume growing technique within the extracted vessel endpoint as a seed, for example. This automatic segmentation of the thrombus will enable determination of the subsequent analysis of its length and morphology, surface area, and so on.

The automatic segmentation of the thrombus enables the subsequent analysis of its morphology. Within this context, thrombus length and thrombus surface area may be determined using the above technique will determine likelihood of early thrombolysis. The thrombus lysis is dependent on the length and/or surface area and volume of the thrombus. Therefore, the tool 22 may calculate thrombus length, surface area and volume of the thrombus directly exposed to the blood and thrombolytic drug using the imaging data.

This automated method of determining thrombus morphology may be validated against CT data from a large patient dataset. The automatic thrombus segmentations developed by tool 22 may be compared with manually delineated thrombus segmentations from expert independent observers using similarity metrics like the Dice coefficient and the Hausdorff distance. This validation technique may be used to improve on the thrombus segmentation technique and the automated thrombus segmentation technique. Similar techniques may be used to determine thrombus size and morphology using MRI or TCD or other imaging modalities based on availability.

Thrombus Permeability

A thrombus that is permeable to blood (i.e. porous) may be more likely to dissolve quickly with thrombolytic drugs compared to a non-permeable thrombus. The system uses novel techniques to automatically determine the permeability of a thrombus.

Automatic Determination of Thrombus Permeability Using Contrast Density

The first technique for determining thrombus permeability involves measuring the change in contrast density within a thrombus using mCTA scans or source images of a CTP. Example mCTA techniques are described in International Application No. PCT/CA2013/000761 entitled SYSTEMS AND METHODS FOR DIAGNOSING STROKES, the entire contents of which is hereby incorporated by reference. The location of the thrombus may be determined on multi-phase CTA (as an illustrative example) or other imaging modality depending on availability. Next, contrast density measurements may be taken from the thrombus segment in the time varied mCTA and/or CTP images, and a time density curve is obtained from the region of the thrombus. The more the thrombus region increases in density over time, the more permeable the thrombus is since the contrast is permeating through the thrombus. The rate of increase in thrombus density over the temporal duration of a multi-phase CTA or a CT perfusion is used to automatically determine the degree of thrombus permeability. For example, the degree of thrombus permeability can be presented on a four level scale: no permeability, mild permeability, moderate permeability and extensive permeability, which are then integrated into the algorithm of the tool 22. This is an illustrative example.

Automatic Determination of Thrombus Permeability Using the Occult Antegrade Flow Technique on CT Perfusion The technique for automatically determining thrombus permeability uses CT Perfusion T0 maps to determine the forward flow through a thrombus. CT Perfusion T0 maps measure arrival time of contrast from that in a reference artery (an example is the arterial input function (AIF)) as an arterial reference point in a CT Perfusion processed map. The CTP dataset is automatically realigned with CT angiographic images by tool 22, as described herein, to correct for movement between the scans.

The 3D centerline representation described in herein may be used to define the end points of the thrombus. In a following step, the average map by averaging all the dynamic images of a CTP study will be registered to the corresponding CTA dataset using a rigid 3D transformation. As the average map and perfusion parameter maps are inherently registered with respect to each other, the same rigid transformation will be applied to the T0 perfusion parameter map so that the corresponding T0 values for the proximal and distal ends of the thrombus can be determined. The distal end of the thrombus is identified by a higher T0 value than the proximal end. Starting from the distal end point, the vessel centerline is traced within a volume of interest in the average map with the distal endpoint as the center and the corresponding T0 values are extracted. The T0 values and corresponding distances to the distal thrombus end point are then used to calculate the slope of this profile using a regression analysis. The automatic method of determining thrombus permeability may be compared to a semi-automatic method using Bland-Altman plots for validation.

If the difference in T0 values between the proximal and distal end of the thrombus is small (e.g. <2 seconds) and the slope of serial T0 values distal to the thrombus is significantly positive. This generally means there is forward flow through the thrombus, meaning the thrombus has some degree of permeability. The difference in T0 values between proximal and distal end of the thrombus and the value of the slope of the line of best fit of T0 values in the artery distal to the thrombus may be used to indicate the degree of forward flow through the thrombus, and thus the degree of thrombus permeability, which can again be presented on a scale.

In FIG. 3, each of images 30 and 32 illustrate a CTP T0 map. In image 30, the location of the thrombus and the distal end of the thrombus is determined on CT angiography. In image 32, points are marked at the proximal and distal end of the thrombus as well as along the artery distal to the thrombus. In image 34, the above CT-angiography image is overlayed over a CTP T0 map and T0 values calculated, where a visual indication of the overlay may be provided as part of decision support. The graph 36 to the right shows example calculations that help determine thrombus porosity. A positive slope and a small difference between T0 values proximal and distal to the thrombus indicate a porous thrombus (FIG. 3 at image 30). A negative slope and a large difference between T0 values proximal and distal to the thrombus indicate a non-porous thrombus (FIG. 3 at image 32).

Collateral Blood Flow

The tool 22 may also use $T_{Max}$ (e.g. T0+½ of Mean Transport time) map from a CTP scan to quantitate collateral flow more precisely. A smaller $T_0$ value indicates that flow to the ischemic region is taking a more direct route while a smaller MTT indicates that once arrives at the ischemic site, blood is flowing relatively quickly through the region. This method of quantitating collateral flow using $T_0$ or $T_{Max}$ maps may use similar measurements of thrombus permeability. A negative distal artery profile slope as described herein may indicate retrograde flow through collaterals. The degree of the slope and the difference between proximal and distal thrombus interface $T_0$ values provide a quantitative assessment of collateral status. A smaller $T_{Max}$ value in the distal thrombus interface may indicate better collateral flow, for example. Good collaterals may be associated with higher likelihood of the thrombus dissolving early with the thrombolytic drug; poor collaterals reduce the likelihood of early dissolution of the thrombus with the thrombolytic drug significantly. The tool 22 may use automated collateral assessment from either multi-phase CTA or the $T_0$ maps along with thrombus length and thrombus surface area to determine probability of dissolving early with the thrombolytic drug. The tool 22 may also track and determine $T_{max}$ which may be defined as the sum of $T_0$ and one half of mean transport time (both generated by the software) as an additional parameter to characterize collateral flow. A smaller $T_{max}$ value may indicate better collateral flow. Accordingly, embodiments described herein may calculate the collateral flow using one or more $T_{max}$ values.

The probability of early dissolution of thrombus using the thrombolytic drug may be modeled by the tool 22 as a function of thrombus morphology and collateral status parameters (described herein) using logistic regression analysis, random forest classification, regression model and a trial patient dataset. Using logistic regression and a likelihood ratio based approach, the tool 22 may model the probability of achieving early recanalization as a linear function of the imaging parameters identified above. The random forest classification and regression model is a nonparametric high-level machine learning technique useful for variable selection and prediction. The predictive performance of this model will be assessed using the out of bag (OOB) error. Random forest regression and classification may provide a predictive tool that makes less stringent assumptions about data distributions, sample size, and predictor correlations than logistic regression analysis.

The prediction models derived from logistic regression analysis and random forest classification and regression models may be validated using an internal validation approach and the same trial patient dataset.

For internal model validation, cross-validation may be used by the tool 22 to adjust for optimism bias (the difference between the prediction error for the entire cohort and the training cohort). The tool 22 may implement one or more training stages for machine learning. The tool 22 may also conduct external validation using combined data from other recent patient datasets. Using the models derived and internally validated in our study data, the tool 22 may obtain the predictive accuracy of models using the external validation data. A model with high prediction accuracy may be used as input into the tool 22.

Additional Imaging Factor: The Risks Involved with the Thrombus Busting Drug Vs. Endovascular Treatment The third imaging factor quantifies the risks involved with administering the thrombolytic drug to the patient compared with the risks of the endovascular procedure.

Risks Involved with Administering the Clot Busting Drug

A serious risk involved with administering the thrombolytic drug is bleeding in the brain. A likelihood of a patient bleeding in the brain after receiving the thrombolytic drug may be determined or estimated with a high degree of specificity using CTP images based on the concept of very low blood volume but high vessel permeability. The tool 22 determines the probabilities of bleeding with minimal human involvement using the techniques described herein and other imaging techniques.

For example, the tool 22 may use the non-contrast CT scan images to determine a degree of hypo-attenuation (reduced signal) in the ischemic brain. The affected region for automated analysis may be determined using techniques described herein. There is risk of bleeding into the brain if the patient has a sub-acute stroke i.e. present after >24 hrs (e.g. a long time) from stroke symptom onset with severe ischemia in certain regions of the brain. Determination of sub-acute stroke can be made using imaging. It is to be noted that significant hypo-attenuation on a non-contrast CT scan is often used by expert stroke physicians to withhold the thrombolytic drug from stroke patients. Hypo-attenuation in ischemic brain that is similar to or lower than normal white matter hypo-attenuation may indicate severe or sub-acute ischemia in that region of brain; this is considered a relative contra-indication for use of the thrombolytic drug because of the increased risk of thrombolytic drug-associated hemorrhage. The tool 22 may use the same techniques described herein to automatically determine if such a degree of hypo-attenuation exists in the ischemic region in the brain.

There may be risks for hemorrhage for different reasons. Management decisions may be based on whether blood is sub-arachnoid or parenchymal, if sub-arachnoid, what is the source of the bleed, if an aneurysm, the best way to treat it, if an AVM, what is the best way to treat this, if parenchymal, and so on. Treatment factors may include for example, age (young, old), location (superficial, deep), underlying lesion (avm, tumour) or no underlying lesion (hypertension and amyloid angiography), active bleeding or not, availability of neurosurgical treatment options and medical options.

A large brain region with very poor collaterals is associated with a higher risk of thrombolytic drug-associated hemorrhage. The tool 22 may also use information derived from automatic assessment of collateral status in different regions of the ischemic brain described herein to determine risk of bleeding into the brain. The tool 22 may also use CT perfusion to analyze various perfusion parameters including: permeability surface-area produce (PS), very low cerebral blood volume (vlCBV), very low cerebral blood flow (vlCBF), mean transport time (MTT), and $T_{max}$. These CT perfusion parameters, when available, may also be predictive of the risk of the bleeding into the brain with the thrombolytic drug.

Risks Involved with the Endovascular Procedure/Factors that Reduce the Likelihood of a Successful Endovascular Procedure while Prolonging the Time Taken for a Successful Procedure.

Several factors can increase the risk of the endovascular procedure or make the administration of the procedure more difficult. These factors include severe tortuosity of neck blood vessels, the presence of significant carotid atherosclerotic disease that might prevent passage of an endovascular catheter, and the presence of extra- or intracranial dissection. The tool 22 may use CTA head and neck imaging to quantitate each of the above parameters. Each of these variables prolong the time taken to achieve a successful endovascular procedure or may completely preclude a successful endovascular procedure. Output from this quantitation may be used by the tool 22 to generate output results for decision support.

Various alternative technologies may be used to receive imaging data for the patient. For example, there may be a CT scanner in the ambulance or other emergency transport vehicle. There may be the capability to be fully integrated in the ambulance based system, for example. The input factors may remain the same as described herein. However for output based on the distance to the primary care centre to the tertiary care centre (and the corresponding estimated transmit time at step 206), the DI DO (door in door out) time at the primary care centre and previously described factors such as likelihood of clot dissolving with IV tPA, may be used by the tool 22 for generating output for decision support to assist with decisions regarding bypassing the primary care centre or not.

As another example, the imaging data may be received from cross sectional imaging technology in the angiography suite. This can be done in different ways. For example, there may be hybrid rooms where there is either a CT scanner or an MR scan built in beside the angiography suite. As further example, there may be cross sectional imaging in the angiography suite itself. A patient may go straight from emergency room to the angiography suite, and have the imaging performed to generate the brain scan images. The tool 22 outputs the decision to a display device in the angiography suite (or via a remote connection) and depending on the decision made, the care providers start the procedure. Here in the tool 22 may implement the process described herein with a few variations. In case an option (which may be common) is being used then one cannot obtain typical perfusion maps. Perfusion maps may give their output differently (called PBP). These could be used as a surrogate for irreversibly infarcted tissue, for example. Also it is likely that the time between imaging and reperfusion may be dramatically reduced in this scenario which would be built into the tool 22 configuration.

For patients getting transferred, the imaging at the primary care centre may provide guidance regarding whether a detailed repeat imaging is required at the CSC or not. It may be based on the following factors: amount of irreversibly infarcted brain on original scan, quality of collaterals, and time elapsed in between the imaging and the treatment to factor the concept of 'shelf life of imaging'. Rather than using a fixed value, this may be flexible based on factors noted herein. If the overall time is short and the collaterals are good, the tool 22 may provide decision support regarding bypassing the CT scanner and MRI scanner and going straight to the angiography suite and possibly performing a basic head CT scan to rule out hemorrhage or other bleeding risks. This is an example onl and other imaging technologies include TCD, US, electrical impedance plethymosgraphy, spectroscopy, and so on, may be used.

At step 206, the tool 22 determines an estimated transport time to transfer the patient to a treatment facility. The tool 22 may also determines an estimate treatment time until the patient can receive the reperfusion or other treatment at the treatment facility after transfer.

Input Factors—Time

Another general input factor in determining whether a patient should be transferred is the time factor that may be based on multiple variables that correspond to time estimates. The time factor takes into account the time required to pragmatically transfer the patient to the tertiary hospital from the primary hospital, as well as the time required to open the vessel in the patient's brain through the endovascular thrombectomy procedure once the patient arrives at the tertiary hospital. Various factors may be taken into account in determining the time, including the distance between the hospitals, the time of day, weather, traffic, availability of transfer vehicles and trained personnel, availability of physicians who can perform the endovascular procedure at the tertiary hospital, the medical status (stability) of the patient, and more. These factors may have a baseline or default value set for a particular site e.g. if the average travel time to the tertiary health facility is approximately 90 minutes (including patient transfer to ambulance) then this would be a fixed variable for that particular site. However additional factors e.g. traffic issues or weather would allow the site to change this.

Automation

The tool 22 automates the collection of information regarding the previously described factors and, at 208, determines a patient assessment profile using the system model. The patient assessment profile may be generated by tool 22 using the patient brain imaging profile, the estimated transport time, and the estimated treatment time. The patient assessment profile defines a patient treatment protocol indicating a probability of an expert treatment decision for transferring the patient to the treatment facility and providing the reperfusion at the treatment facility. The patient assessment profile defines a visual representation for display on a display device, where the visual representation may visually indicate the thrombus morphology and an estimated quantity of brain tissue that will likely become irreversibly infarcted after the estimated transport time and/or the estimated treatment time using the rate or the estimated quantity of patient brain tissue that likely will become irreversibly infarcted at the future time.

At 210, the tool 22 may be refined with additional data about the patient and other clinical and imaging data using machine learning, feedback, and validation data, as will be described herein. For example, FIG. 22 at 2218 references validations and feedback from multiple clinical data and imaging data sets as well as expert physician decision data.

At 212, the tool 22 outputs decision support information to help the end-user (i.e. the physician in the primary hospital) make an expeditious and appropriate decision on the triage of his/her patient, i.e. to decide whether the patient should be triaged from the primary hospital to the tertiary hospital for the endovascular procedure. The output may include the visual representation of the patient assessment profile on a display screen as described herein. The information input into the system may be collected using as little input from the physician as possible given an emergency situation and time limitations. Physician/health care personnel involvement may generally be limited to providing clinical information such as the patient's age, stroke severity, stroke onset time and side of stroke involvement.

Decision Support Tool

Figure 22:
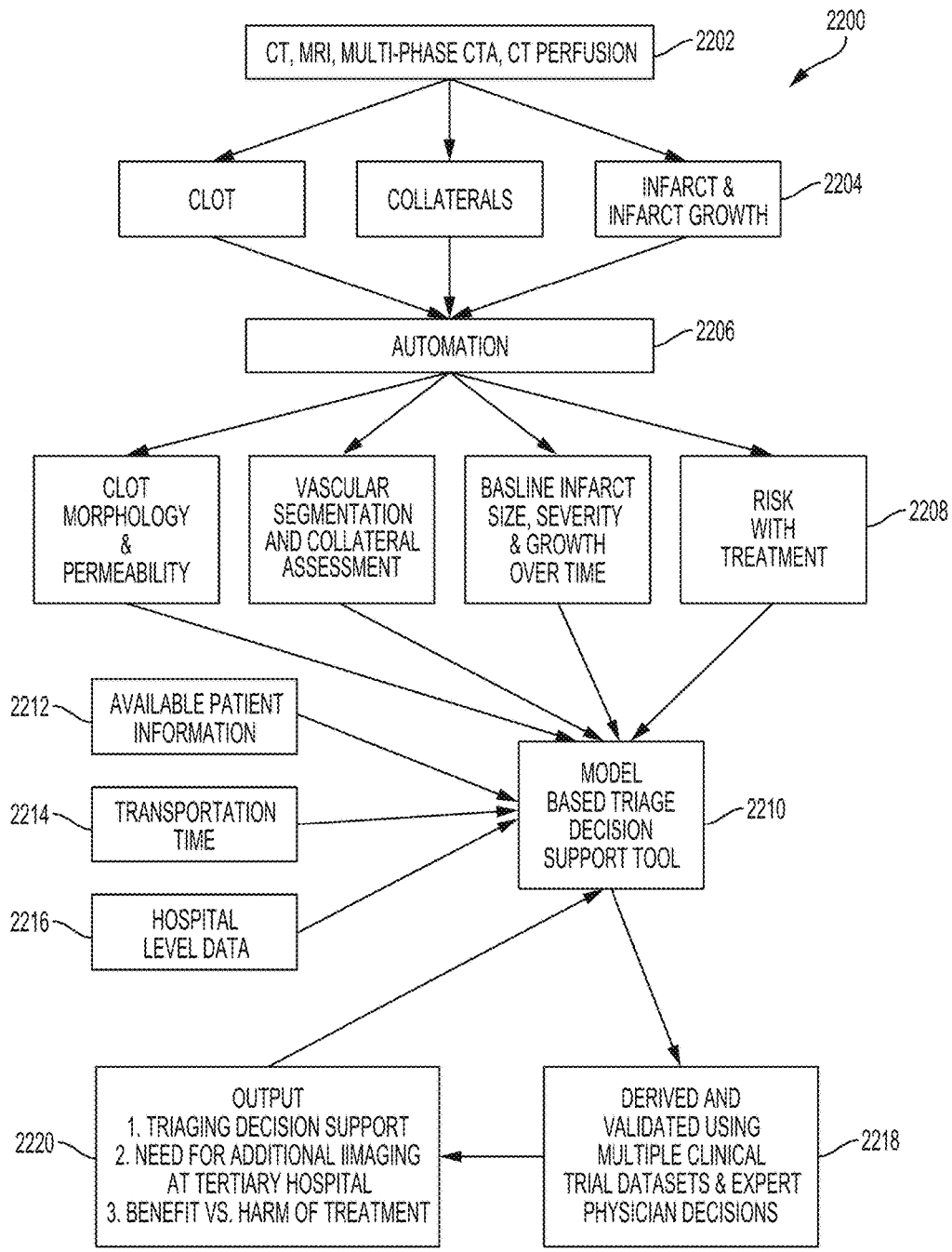
FIG. 22 is a flow chart diagram of the development process for an automated triaging decision support tool according to some embodiments.

FIG. 22 is a flow chart diagram of the development process 2200 for a tool for automated triaging decision support according to some embodiments.

At 2202, the tool 22 (or separate and connect system component) receives imaging data from one or more imaging modalities such as CT, MRI, multi-phase CTA, perfusion, and so on. Other clinical data may also be provided to tool 22. Examples of image data is described herein.

At 2204, the tool 22 may process the imaging data to generate an intermediate data set regarding a thrombus, collaterals, infarcts, and infarct growth in the brain scan images. Examples of image processing is described herein.

At 2206, the tool 22 automatically constructs or refines the data set and generates decision support information as described herein. The tool 22 automates the collection of information at 2204 regarding the previously described factors to determine a patient assessment profile. The patient assessment profile may be generated by tool 22 using the patient brain imaging profile, the estimated transport time, and the estimated treatment time. The patient assessment profile defines a patient treatment protocol indicating a probability of an expert treatment decision for transferring the patient to the treatment facility and providing the reperfusion at the treatment facility.

At 2208, the tool 22 determines additional patient metrics such as thrombus morphology, permeability, vascular segmentation, collateral assessment, baseline infarct size, severity and growth over time, and risks for treatment. This data is provided at 2210 to further construct or refine the system model.

The tool 22 receives available patient data including additional clinical and imaging data (at 2212), data regarding transportation time (at 2214), and data regarding health care facilities including available treatment services and treatment times (at 2216). The data is also provided as input to refine data sets used by the tool 22 to generate output results for decision support.

At 2218, the tool 22 further derives and validates the system model using additional clinical datasets and expert physician heuristics.

At 2220, the tool 22 generates and provides output data including triaging decision support, a flag that additional imaging is required, and risk analysis. This information is also used by the tool along with physician feedback to further refine the system model continuously. For example, different weight factors may be linked to different input factors to provide an indication or assessment of their importance. As an example, if a large portion of the brain is irreversibly infarcted then transfer and treatment may be futile regardless of the values for other input factors. As another example, if the patient has good collaterals this may be linked with a high weighting to indicate the importance of this data value when deriving decision support as treatment may be more likely to provide a good outcome. In contrast, a patient with poor collaterals may be a very relevant input factor as successful treatment may be less likely. Accordingly, different input factors may be assigned different weighting factors based on their impact or relevance to the decision support output results. As noted, feedback from expert physicians may be used to refine the weightings and validate the output results. Further, additional imaging and clinical data sets may be used to refine the tool 22. Various other examples are described herein. The weighting and refinement enables the tool 22 to adapt to different data sets, feedback and results as received as part of machine learning. This creates a feedback loop for refinement of the tool 22.

Other types input information detailed herein may be provided as input data into the system model to determine the probability that a patient will be triaged by an expert stroke physician. Each of the input factors described, specifically the clinical, imaging and time factors are input into the system. The system model may be built in the following illustrative example manner.

For heuristics, expert stroke physicians may independently examine clinical data and output from the automated imaging techniques described above i.e. probability of early dissolution of thrombus with the thrombolytic drug, estimated baseline infarct volume and infarct growth over pre-specified time periods (60 mins, 90 mins, 180 mins and >180 mins) in a randomly selected sample of many 250 patients from multiple a trial patient dataset. The expert will examine each dataset in a random order. Unique to the model building exercise, the experts will also be provided with incomplete information (e.g. A missing CT perfusion scan or a missing non-contrast CT scan or unknown time of stroke onset) to determine how a triaging decision is made in the absence of some piece of information. Each expert will then decide whether a patient should have been triaged or not using the available information. The tool may use predictive machine techniques to assess a probability of agreement among the expert decisions at each step using an unweighted Fleiss Kappa statistic, for example. This may estimate a measure of the extent to which agreement among the experts exceed what would have been expected if they all made their ratings completely randomly. Consensus decisions may be input into the model.

As another step in building the tool 22, the probability estimates of early dissolution of the thrombus with the thrombolytic drug, baseline infarct volume and estimated infarct volume at the time the patient reaches the tertiary hospital from the community hospital and patient-specific information like age, stroke severity, and baseline functional status whether the patient has contra-indications for alteplase or other thrombolytic drugs (e.g. Is on a blood thinner or has a bleeding disorder) will form input variables of a random forest classifier and regression model. The dependent variable for these models will be the triaging decisions made by experts. Wherever experts disagree, the tool may use an adjudicated consensus triaging decision will be used. The accuracy of the predictive model for triaging will be assessed using the out of bag prediction error from the random forest regression. The tool 22 output results may be validated using a 10-fold cross-validation methods to determine the accuracy of these models in predicting the triaging decision made by experts. Using the models derived and internally validated from the trial patient dataset, the tool 22 may also obtain the predictive accuracy of this risk prediction model using an external validation dataset. This predictive accuracy so determined will be available to all users in an earlier version of the tool 22 or system model.

The tool 22 may use transportation time data available through regional health services and geographic information systems (GIS) to determine the time to transfer the patient. The final model will also use any available regional health data like median door-in-door-out time in community hospitals and median door to groin puncture and reperfusion times in multiple tertiary hospitals within a 500 km radius of the community hospital and staffing patterns in surrounding tertiary hospitals (i.e. availability of specialists 24 hours 7 days a week), to provide the physician at the community hospital guidance on which hospital to refer the patient to increase chances of good outcome.

The tool 22 may also have the capability to modify the output based on missing or non-contributory information. For example, if the patient has a regular non-contrast CT head scan, a multi-phase CTA scan, and a CT Perfusion scan, but the CTP scan is degraded by patient motion and therefore unusable, the tool 22 will recognize that the CTP scan is non-contributory and modify the output of the model accordingly. In another example, if stroke onset time is missing, or a hospital is not able to perform a CTP or mCTA scan, the model will account for this while providing an output constrained by that condition. In addition, the tool 22 will be able to incorporate multiple imaging technology types in addition to CT scans, such as MR images, transcranial Doppler ultrasound, electrical impedance spectroscopy or other brain and neurovascular imaging technology that is or becomes available. The tool 22 will recognize the available information and keep or reject imaging information depending upon quality and type, and modify the output of the model accordingly. The tool 22 may give a confidence interval (or error rate) on the output. Based on testing of the model it is possible that missing critical information may dramatically increase the error rate. Alternatively it is also possible that in many situations e.g. absence of CT perfusion, information may not dramatically affect the output.

The tool 22 may continue to refine the model at step 210 (shown as feedback loop 2210, 2218 and 2220 of FIG. 22) using machine learning and improve its predictive accuracy using new information that will be available when the product is being tested real time and when the product is in clinical use. This continuous feedback process will happen so that tool 22 will allow community hospitals and physicians to provide feedback information on appropriateness of triaging decisions made using the tool 22. The community hospitals will in many cases, use feedback they receive from tertiary hospitals that they referred patients to. In addition, the model will be validated every two years with new trial datasets that are available nationally and internationally. The patient assessment profile may be updated at 208 using the refined system model. Further, future determinations of patient assessment profiles will used the continually refined system model which may improve accuracy over time and use. This may be shown in FIG. 22 as a feedback loop from 2218 and 2220 to 2210.

As described, the tool 22 may refine as additional data is available. The tool 22 may provide an incremental prediction of outcome as data become available. For example, as new data is available, such as clinical, historical, observed, or from imaging devices, the new data will arrive into the tool 22 in a necessarily sequential series over time (e.g. over 30 minutes). The output then is continually updated as new data become available. The tool 22 can then trigger a threshold recommendation to treat or to transfer (or both) the patient before further data are gathered. Other example feedback may be provided to continuously refine and update the output results of tool 22. The treating team will have the ability to change settings on the output based on their overall treatment strategy, distance and relationship with the care facility. This is especially relevant e.g. if the paramedic team stays with the patient while the decision is being made. In that case, the sooner the decision is made the less is the wastage of time of an extremely valuable resource (the paramedic team). So the team at the primary care facility, could decide if the output is above say 80% (as an illustrative example) for transfer, the technician may stop all further work-up and focus our energies on the transfer. This may become relevant in the extreme situations. For example, a 40 year old comes in with a massive stroke onset 1 hour ago. In this case the only information that one needs to cross the threshold of 80% is a plain CT head to rule out a hemorrhage. This may be implemented using the weighting factors. This information goes over to the tool 22 and immediately the software shows the output as green or good as it crossed the pre-determined threshold set up by the treating team. All further imaging work up is immediately stopped based on the output. As another example, consider a 65 year old otherwise healthy person comes in with a severe stroke (NIHSS 18) who has known atrial fibrillation and is on Coumadin. INR performed 4 days ago was 2.7. This patient has no treatment options at the primary care facility. As such very little information would be needed to make transfer besides a scan to rule out hemorrhage. These are illustrative examples of the feedback and weighting process.

The tool 22 may modify itself to various geographical locations, countries and health systems using machine learning from information that is available from each of these systems. Thus the system model will adapt itself to the health system, province, country or geographical disposition in which it is located. This model improvement exercise will follow the same principles outlined herein. Error rates are also built into the tool 22 to give an overall degree of confidence to decision making.

The tool 22 may also adapt using machine learning algorithms techniques that may adapt to changing imaging technology and the accuracy and validation of various imaging parameters; changing transportation infrastructure; organization and speed of treatment at the tertiary centre; improvement in endovascular treatment resulting in faster and more robust reperfusion; and the development of adjuvant therapies (such as neuroprotection e.g. hypothermia and various pharmaceutical agents) that can be administered during transit or transport that can slow down the rate of brain death.

Referring back to FIG. 2, at 212, the tool 22 may output the patient treatment protocol as clinical decision support information for display on a display device, for storing on a storage device, or for transmission to another processor using a transmitter. These are example outputs showing illustrative tangible results that may be provided by tool 22. For example, a visual representation may be provided on the display. This may align with step 2220 of FIG. 22. The output data may be updated using feedback, additional data, machine learning and other refinement processes implemented by tool 22.

Output

The output of the tool 22 can be tailored to the specific needs of the end-user. For example, some end-users may only want a yes/no decision on whether to transfer the patient. In this case, the tool 22 may provide a yes/no decision along with confidence intervals on the precision around the decision. The type, amount and format of output may be configurable by a specific user or health care facility. On the other hand, for end-users who prefer to have more information, the tool 22 may also provide the following illustrative example information:

a) the amount of irreversibly infarcted brain tissue;
b) the amount of tissue that is likely to die by the time the patient reaches the tertiary hospital and undergoes the endovascular procedure;
c) the eloquence of the tissue (weighting by functional importance of the brain tissue at risk) that is likely to die by the time the patient reaches the tertiary hospital and undergoes the endovascular procedure;
c) where the thrombus is and how large (eg. volume) the thrombus is;
d) the probability that the thrombus will dissolve early with the thrombolytic drug;
d) the risks of bleeding into the brain with the thrombolytic drug; and
e) the probability of success with the new endovascular procedure.
f) The need to repeat a brain scan at the tertiary center.

Case Scenario

The following case scenario is provided as an illustrative example. An 80-year-old male was at a grocery store at 9 pm when he fell down. Onlookers tried helping and found he was not able to speak or move the right side of his body. They called the paramedics who reached the store within 10 minutes. The paramedics diagnosed stroke and immediately took the patient to the nearest community hospital that was 20 miles away. A doctor in the Emergency Room saw the patient within 45 minutes of stroke symptom onset. The patient had a CT scan with CTA and CTP of the brain within the next 5 minutes.

The doctor now has to make a clinical decision. He needs to decide if the patient should be treated at his hospital with an intravenous thrombolytic drug or whether he transfers the patient to the nearest tertiary care hospital. This tertiary care hospital has facilities to remove the thrombus using the new endovascular procedure; the hospital however is 50 miles away and will take around 90 minutes to reach. Besides, he will have to spend another 15-20 minutes trying to contact the specialist there before he can make a decision to transfer the patient to that hospital. The doctor also does not entirely understand the risks of treating the patient with either the thrombolytic drug locally or with the new procedure at the tertiary care hospital. He only sees such stroke cases infrequently he does not have a radiologist specialized in reading such scans at his hospital at 10 pm that night. The family accompanying the patient also wants to understand the risks and benefits with all options.

In a normal scenario, the following outcomes may be likely:
A) The doctor tries to contact the specialist at the tertiary hospital. He is able to contact the specialist in 10 minutes. The specialist wants to know clinical details on the patient and wants to look at the brain scans. The doctor uses a sophisticated tele-radiology solution to have the specialist at the tertiary care center look at the scans. The specialist takes another 20 minutes to access this system and convey a treatment decision to the doctor. It is already 30 minutes after the initial CT scan. Treatment and transfer are delayed by 30 to 40 minutes.
B) The doctor is taking a lot of time trying to contact the specialist. The family is increasingly frustrated and wants to know why there is delay. The doctor decides to administer the thrombolytic drug and transfer the patient to the tertiary care hospital. After the drug is administered and the patient is being transferred, he hears from the specialist. The specialist tells him the scans suggest that sending the patient to the tertiary care hospital will be futile and the risk of bleeding in the brain may be high.
C) The doctor decides to give the thrombolytic drug 30 minutes after the baseline scans after talking to the specialist. The specialist tells him to transfer the patient to the tertiary care hospital. After reaching the tertiary care hospital, the specialist discovers that the thrombolytic drug has dissolved the thrombus and the patient does not need the endovascular procedure. The specialist now transfers the patient back to the community hospital. Lots of resources are spent and the family is frustrated that the physicians did something futile by taking the risk of transferring the patient when the weather was bad.

In the above scenarios, the tool 22 can help in this and many other situations by guiding the community physician in making the correct decision quickly. The tool 22 may tell the community physician if the patient has had a stroke, how much brain it has involved, whether the patient would benefit from getting the thrombolytic drug, if the patient would benefit from being transferred to a tertiary hospital and what is the likelihood of the patient benefiting from either the thrombolytic drug or such a transfer. The community physician can be increasingly confident of his decisions; he can call the tertiary care hospital after he has made appropriate decisions, thus not wasting time initiating vital treatment decisions. He can explain to the accompanying family the risks and benefits of his decisions. The community physician is now capable of making decisions that would only otherwise be made at a highly specialized center. The tool 22 has helped bridge the knowledge gap and has helped the patient by getting him access to the right treatment expeditiously (significantly quicker and at a fraction of the cost of expensive tele-radiology solutions).

The output can be provided on a display device and in a format of choice by the team and/or the individual based on health facility configurations. Expected commonly used formats, singly or two or more concurrently, could be
  Email attachment (to the individual or the whole treating team)
  Texting Text messaging
  Web-based system of display (e.g. Alternative apps or applications such as Whatsapp™ or other messaging apps or specialized products for this purpose)
  Dedicated hospital based computers through a virtual private network (VPN)
  Simultaneous consulting mechanism to a physician at the comprehensive stroke center by providing them with the data The output would have the requisite level of anonymization to meet HIPAA guidelines for anonymity to meet relevant privacy legislation, such as the United States, Health Insurance Portability and Accountability Act (HIPAA).

Additional strategies would be in place to prevent error of patient recognition by the team.
  This could mean direct communication: the two different parts of the team have a phone conversation to ensure correctness of patient data
  An additional anonymization software that creates a new ID which is sent separately from the images.
  Strategies such as password protection.

The output may or may not contain images but may provide visual representations as decision making support.

The output may have the ability to modify factors on the fly e.g. the patient is 72 years old but is extremely healthy and recently ran a marathon using weighting factors that may dynamically adjust based on feedback on provide output results. In the judgment of the medical team, the biological age of the patient is 50 years (much less than the chronological age of 72), the treating team can see the influence of this age change using an adjustment to the weighting factor linked to the input factor for age and the output result will in turn dynamically update on the fly based on the weighting factor adjustment.

Similarly based on the patient's advanced directives and expectations (received by tool 22 as input data factors and patient data), the treating team can adjust the output and change the threshold of acceptable outcome. Accordingly, the output results may be based on threshold values for treatment that may be configured by different care facilities. For example, the output may adjust from 'likelihood of a good outcome' to 'likelihood of a very good outcome' based on the updated threshold values or ranges.

The tool 22 may provide output results that can create a probabilistic model of a scale from very good outcome to bad outcome based on the variables or treatment threshold values that would happen after the decision making (e.g. as feedback). Example variables include:

Time to reperfusion
Quality of reperfusion
Unexpected medical events e.g. Hypotension
Complications of procedure
Complications during recovery e.g. pneumonia The variables may be provided as part of a visual representation for decision support. For example, green may represent good output and red may represent bad output. The visual representation may dynamically adjust as new weighting factors are defined (e.g. using different values) and variables are updated for different input factors. This provides improved decision support as feedback from initial output results may trigger dynamic adjustment of the output to show new visual representations for decision support. The revised output may provide an indication of the importance or relevance of different input variables and weighting factors. This feedback loop may continue to update the output results dynamically to provide improved decision support.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

The hardware may include servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information.

Figure 16:
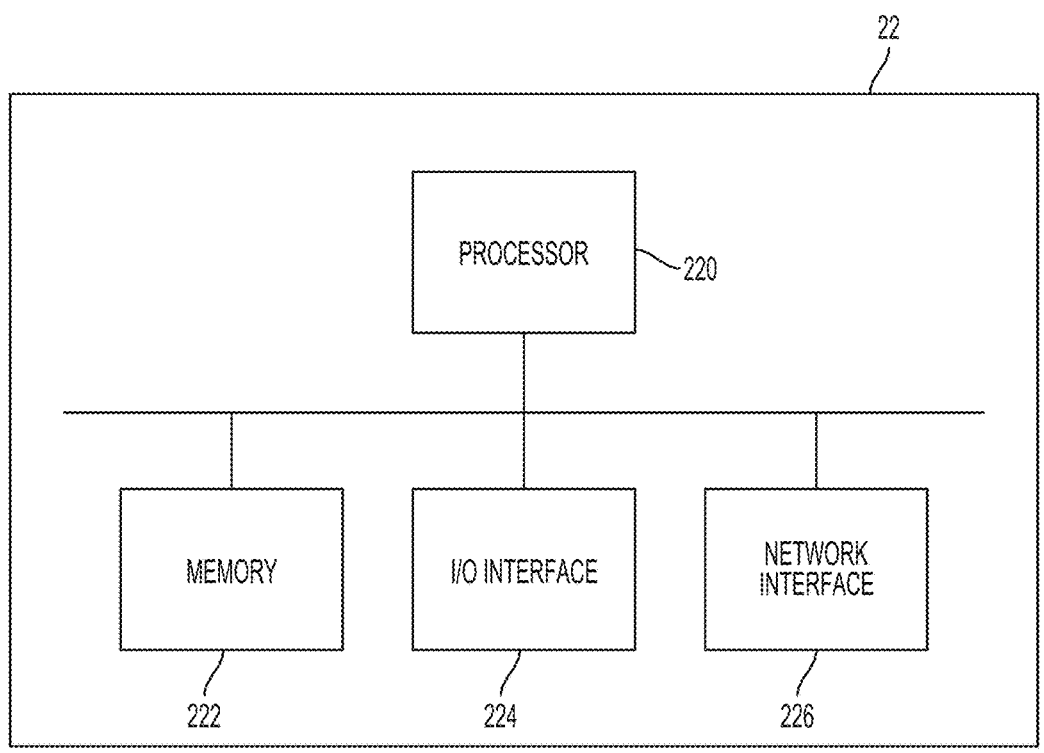
FIG. 16 is a schematic of triage computing tool or device according to some embodiments.

FIG. 16 is a schematic diagram of the triage tool 22 according to some embodiments.

As depicted, the triage tool 22 includes at least one processor 220, at least one memory unit or data storage device 222, at least one I/O interface 224, and at least one network interface 226.

Each processor 220 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof. The processor may be configured to process input data (imaging and clinical factors) to provide output results as described herein.

Memory 222 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. The memory may store weighting factors and input data factors that may be updated based on electronic signals received from I/O interface 224.

Each I/O interface 224 enables the triage tool 22 to interconnect with one or more input devices, such as an imaging device, external memory unit, keyboard, mouse, camera, touch screen and a microphone, or with one or more output devices such as a display screen and a speaker. The I/O interface 224 may provide output results and receive feedback on output results. The interface 224 may connect to an imaging device such as picture archiving and communication system (PACS) for storage and access to medical images from multiple modalities and source machine types. The imaging device may provide local storage, remote cloud based storage, or a combination thereof. Electronic images and reports may be stored and transmitted digitally via imaging device. The universal format for PACS image storage and transfer is Digital Imaging and Communications in Medicine (DICOM). The imaging device may include one or more imaging modalities such as CT and MR and a secured network for the transmission of patient and image data.

Each network interface 226 enables the triage tool 22 to communicate with other components, to exchange data with other components, to access and connect to network resources, to serve applications, and perform other computing applications by connecting to a network (or multiple networks) capable of carrying data. The triage tool 22 may transmit output results via network interface 226 and may receive imaging data via network interface 226, for example. The network interface 226 may provide output results and receive feedback on output results, as described herein. This enables the tool 22 to integrated with various input devices and output devices that may be remote or local to tool 22. The network interface 226 may detect different imaging technologies to adapt tool 22 to interface therewith. For example, network interface 226 may implement different drivers to connect with different imaging modalities.

The triage tool 22 is operable to register and authenticate users (using a login, unique identifier, and password for example) prior to providing access to applications, a local network, network resources, other networks and network security devices. The triage tool 22 may serve one user or multiple users.

Figure 3A:
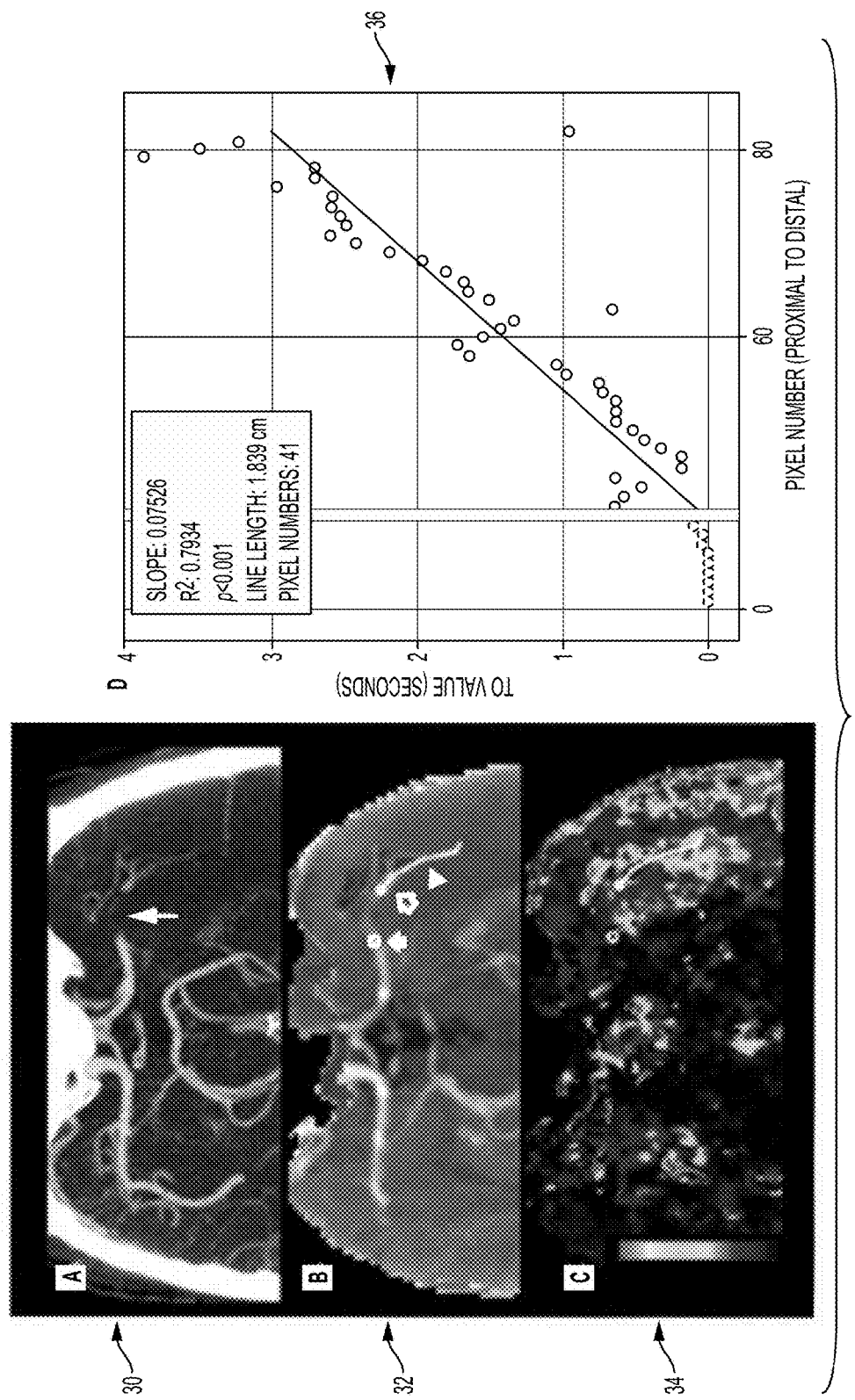
FIGS. 3A and 3B are screenshots of visual representations identifying the presence of a permeable thrombus.

FIG. 3A is a screenshot of a Computed Tomography Perfusion (CTP) map identifying the presence of a permeable thrombus of an interface that may be displayed on display device 102 as an example visual representation of the output data. The visual representation provides CTP T0 maps identifying the presence of a permeable thrombus. A complete occlusion on CTA is shown at image 30 using a white arrow. Regions of interest (ROI) at the proximal thrombus interface are shown image 32 using a solid white arrow and distal thrombus interface are shown at image 32 using a hollow white arrow. The interfaces of the thrombus are shown as visual representations on the CTP average map in image 32. A line profile (white arrow head) is drawn along the silhouette of the artery distal to the thrombus on the CTP average map. The CTP average map co-registered with the CTP $T_0$ map (image 34). A graph 36 plots $T_0$ values against distance (pixel number) along the line profile are then plotted and the line of best-fit determined.

Figure 3B:
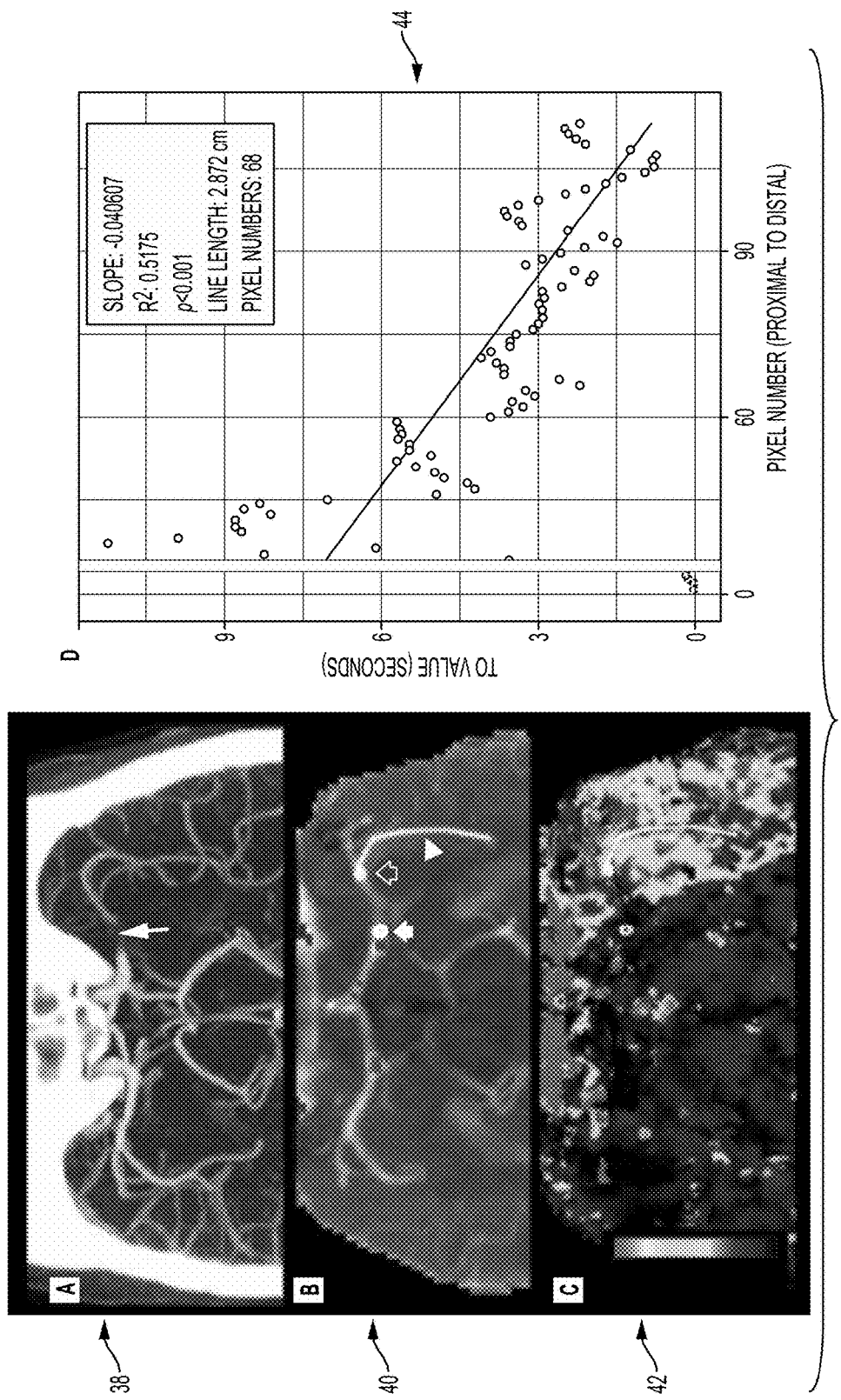

FIG. 3B is a screenshot of a CTP map that may be displayed on display device 102 as another example visual representation of the output data. The screenshot for this patient may identify the presence of a negative artery profile slope (graph 44) suggests presence of retrograde flow distal to thrombus. Other visual representations are shown by images 38, 40, 42.

Figure 4:
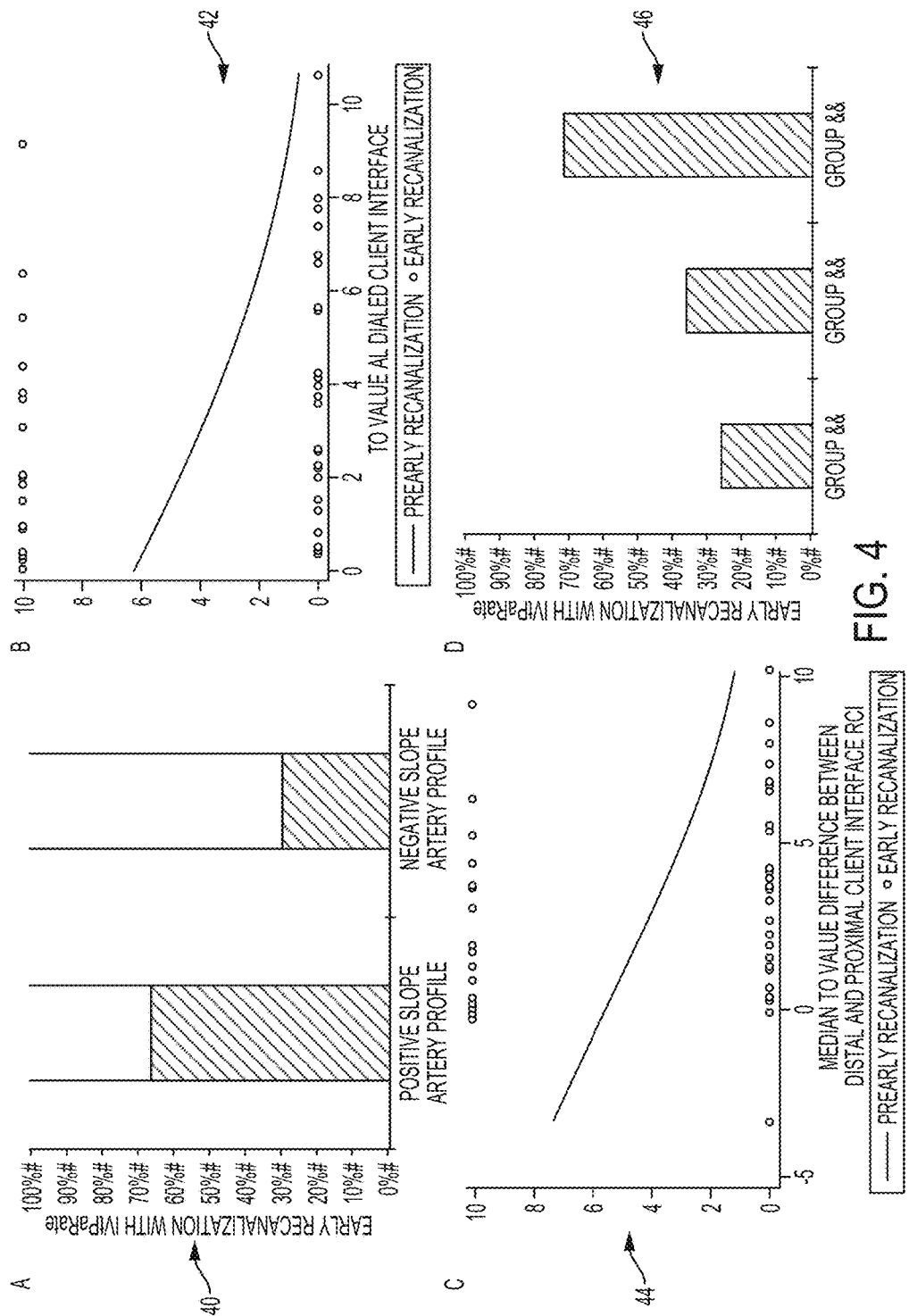
FIG. 4 provides graphs of thrombus dissolution rates based on semi-automated detection of permeable thrombus and automated detection of collateral flow. Automated detection may be used in thrombus dissolution or recanalization rates of the tool.

FIG. 4 provides graphs 40, 42, 44, 46 of recanalization rates. Early recanalization rates with intravenous tPA stratified by different imaging parameters may be measured using CTP $T_0$ maps. An image 40 shows early recanalization rates in patients with positive slope (occult anterograde flow) as compared to negative slope (retrograde flow) artery profile distal to thrombus. An image 42 shows estimates of early recanalization by $T_0$ value at distal thrombus interface. An image 44 shows estimates of early recanalization by difference in $T_0$ value between distal and proximal thrombus interface. An image 46 shows early recanalization rates within the three groups of patients stratified by the imaging parameters.

FIG. 5 is an example a table 50 for a multivariable logistics regression model. The table shows multivariable logistic regression model determining variables associated with early recanalization after intravenous tPA thrombolysis. Group 1 relates to retrograde flow by Artery Profile where $T_0$ value difference between distal and proximal thrombus interface ROI>2 seconds may be the reference group Group 2 relates to retrograde flow by Line Profile OR $T_0$ value difference between distal and proximal thrombus interface ROI>2 seconds. Group 3 relates to anterograde flow by Line Profile and $T_0$ value difference between distal and proximal thrombus interface ROI<=2 seconds.

Figure 6:
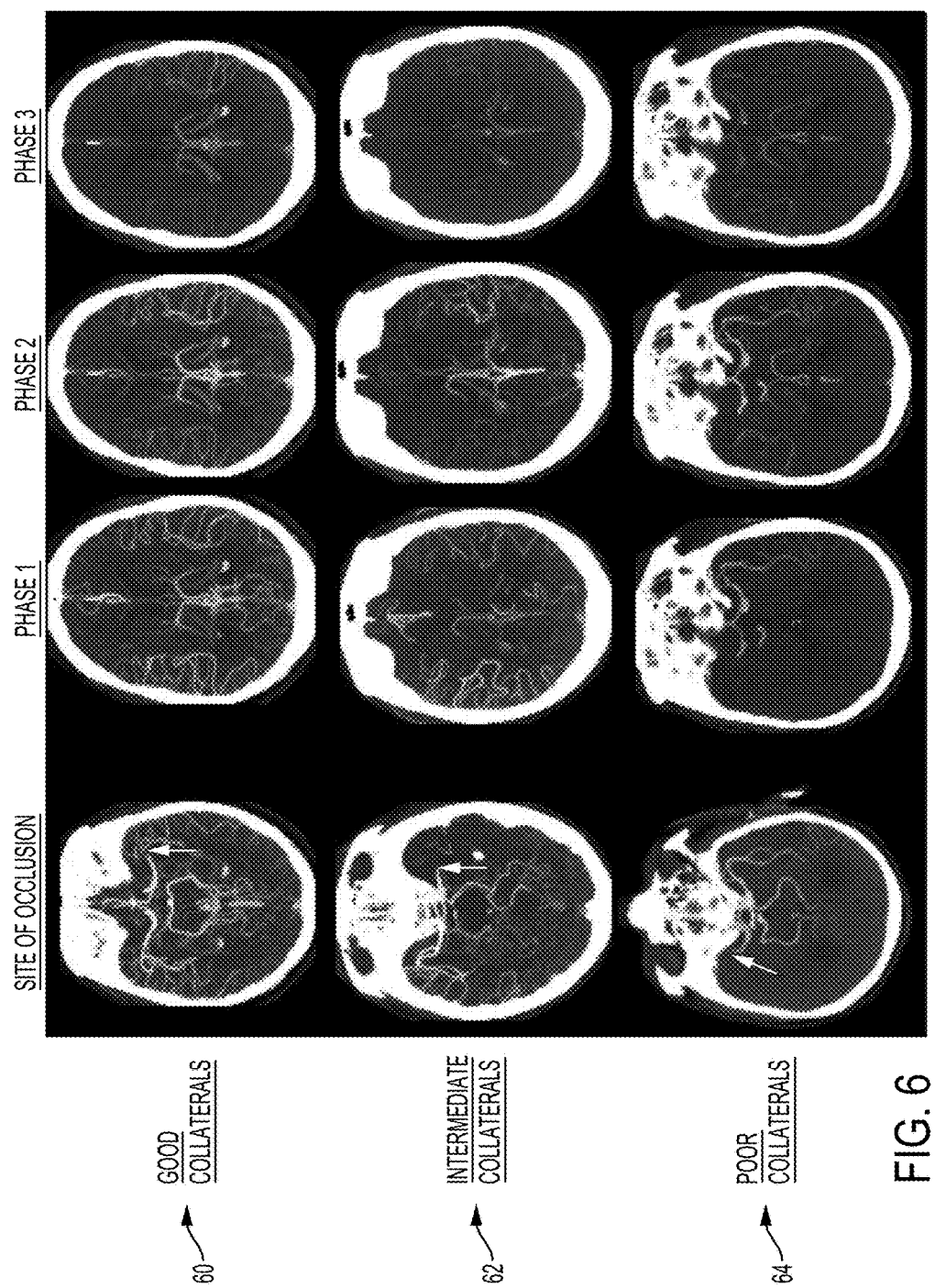
FIG. 6 is a screenshot of a visual representation of patient collaterals.

FIG. 6 is a screenshot of a visual representation of patient collaterals which may be determined by the tool 22 using the imaging data as described herein. The visual representation shows a patient with good collaterals, intermediate collaterals and poor collaterals of an interface that may be displayed on display device 102. The upper panel 60 shows a patient with a left M1 MCA occlusion (white arrow) and good collaterals (backfilling arteries) on multi-phase CTA. The middle panel 62 shows a patient with a left M1 MCA occlusion (arrow) and intermediate collaterals. Lower panel 64 shows a patient with a right M1 MCA occlusion (arrow) and poor collaterals (minimal backfilling arteries) on multi-phase CTA. The interface may receive display screen specifications and re-configure the display of the visual representations in various panels based on the display screen specifications. The panel configuration may be dynamically updated based on requested output results and the display screen specifications as there may be a limited display screen size and a variety of optional output results for decision support.

FIG. 7 is a screenshot of visual representations of image slices from multi-modal imaging. Multi-modal CT imaging at 2 hrs 51 mins post symptom onset with NIHSS of 20 and right hemispherical symptoms. Non-contrast CT shows movement artefact; (panel 70). A proximal right M1 MCA occlusion is seen (panel 72 with reference B-i). The visual representation may relate to mCTA (with three phases) where maximum intensity projections are shown in panel 72 at references B-ii, iii and iv. Collateral circulation is modest with delay of two phases and some regions indicating minimal filling when compared to contralateral side. Perfusion CT $T_{max}$ and CBF maps are depicted in panel 74 at references Ci and ii. CTA and Perfusion CT imaging are congruent for assessment of collateral circulation beyond the occlusion. MR-diffusion imaging at 24 hrs post admission imaging shows the final infarct as hyper intense (panel 76).

FIG. 8 is a screenshot of visual representations of image slices from automatic generation of aerial input functions for use in CT Perfusion. The upper panel 80 shows arterial voxels identified by a k-means classifier based on the area under curve (AUC) of the pixel time-density curve. The lower panel 82 shows a connected 4-voxel artery region (in this case it is a 2×2 voxel region shown in outline) which has the highest AUC among all similar TDCs from the arterial voxels (shown in outline) in this slice as aerial input functions.

Figure 9:
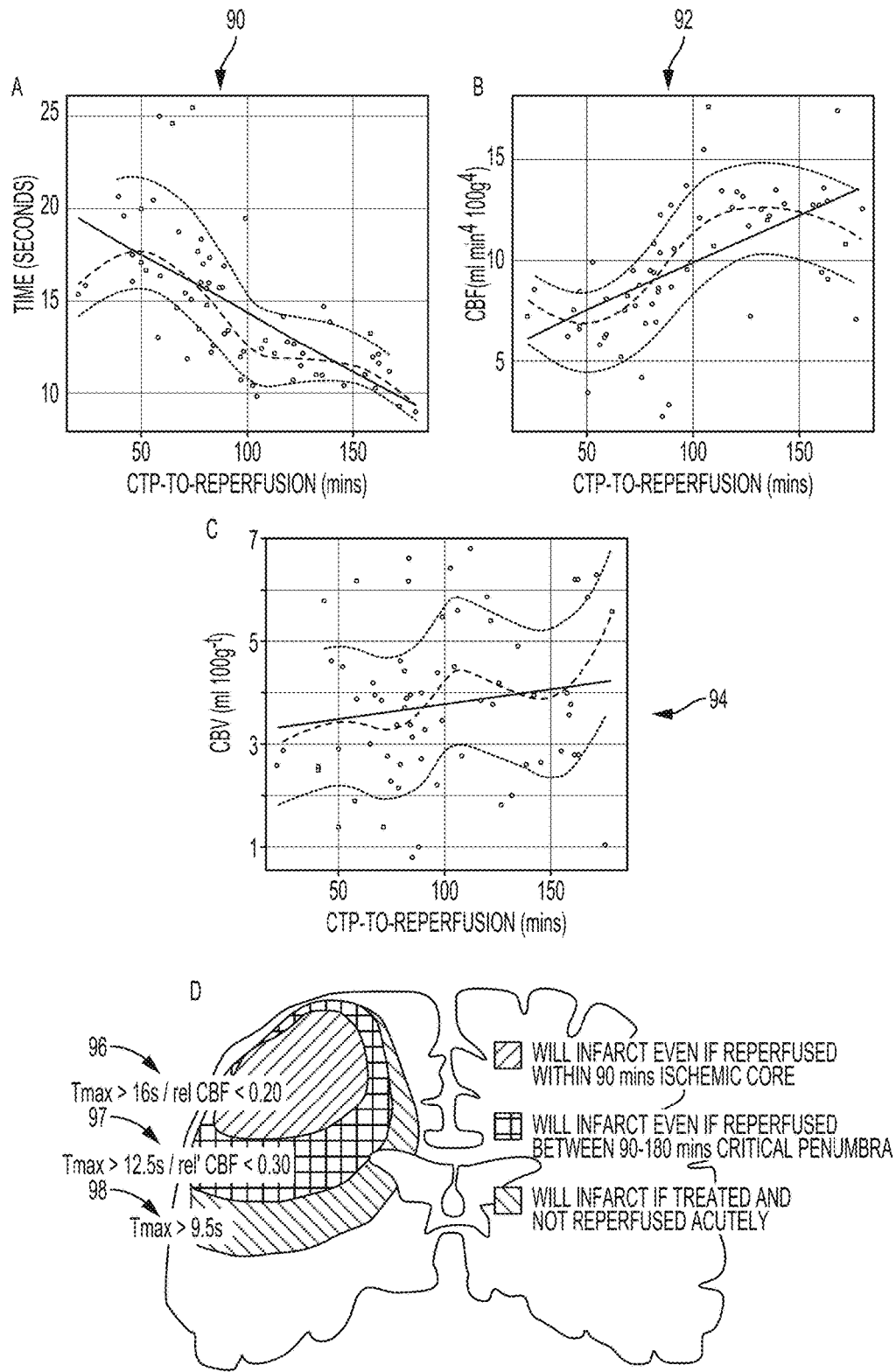
FIG. 9 illustrates visual representations of time-based CT Perfusion thresholds.

FIG. 9 illustrates visual representations of time-based CT Perfusion thresholds charts 90, 92, 94 and a brain view image representing an example of time-based CT Perfusion thresholds that helps estimate future brain infarct over given time data for CTP. The visual representation illustrates charts representing data for CTP to reperfusion. Charts 90, 92, 94 show that the CTP-$T_{max}$ and CBF patient-level thresholds to predict infarction are correlated with the time from CTP-to-reperfusion. The brain view image depicts CTP optimal thresholds for infarction based on time-to-reperfusion for all patients combined (total voxel-by-voxel analysis). The brain view image shows three example visual indications 96, 97, 98 for different values for $T_{max}$. A visual indication 96 relates to $T_{max}$ greater than 16 seconds and CBF less than 0.20. A visual indication 97 relates to $T_{max}$ greater than 12.5 seconds and CBF less than 0.30 A visual indication 98 relates to $T_{max}$ greater than 9.5 seconds.

Figure 10:
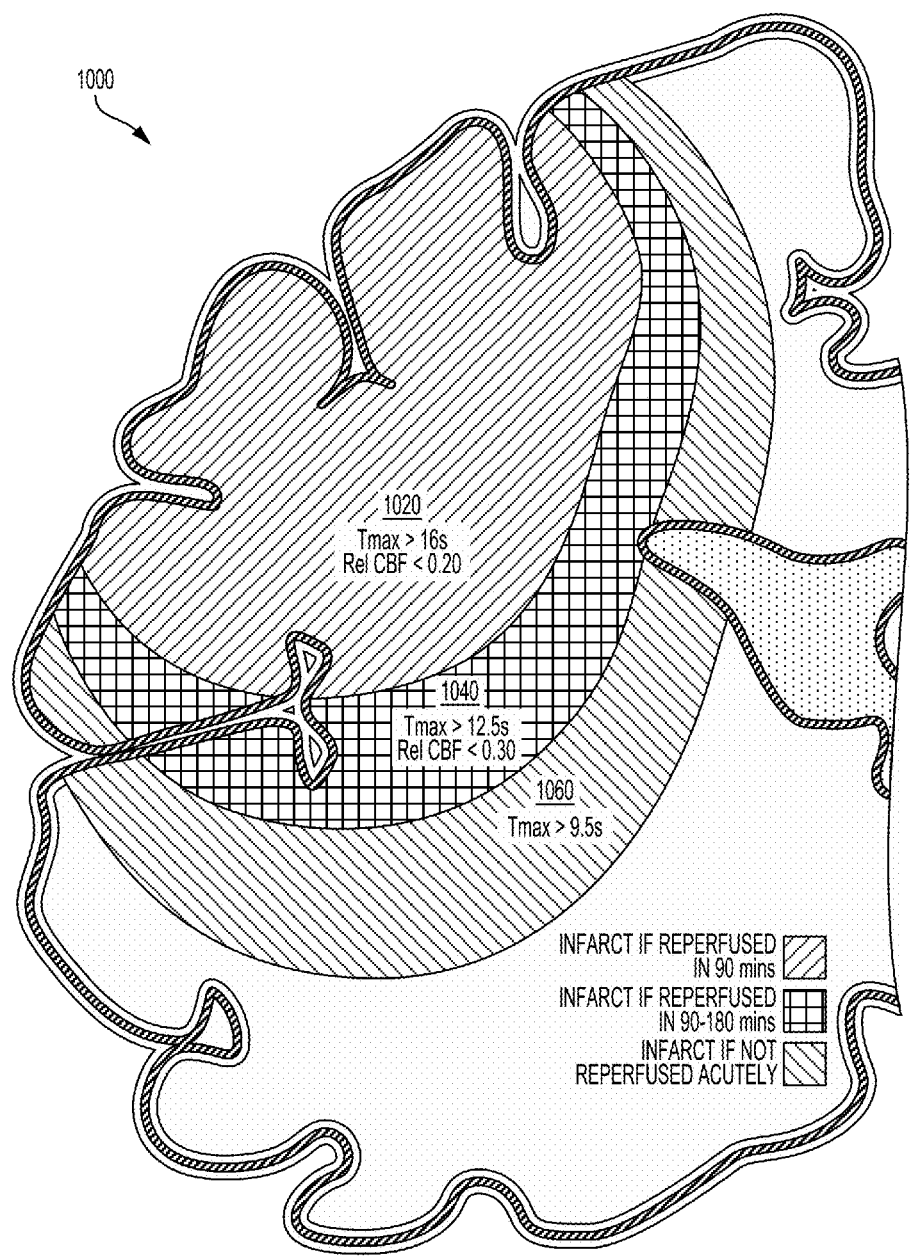
FIG. 10 illustrates a visual representation charts used to construct the time based model for infarct growth using CT Perfusion according to some embodiments.

FIG. 10 illustrates a visual representation of an example time based model for infarct growth using CT Perfusion according to some embodiments with different visual representations 1020, 1040, 1060 for different values for $T_{max}$ and CBF.

FIG. 11 is a screen shot of a visual representation of an image slice of a CTP study according to some embodiments that demonstrates techniques for patient motion correction. This may result from a process to remove unacceptable images for CTP analysis due to motion according to some embodiments. Examples of patient motion are shown in FIGS. 12 and 13. The interface may be displayed on display device. This may be generated using an automated method for removal of z-axis motion correction.

A panel 1100 shows automatic generation of whole brain region of interest in a slice after removal of skull. A panel 1102 shows a time density curve (TDC) of the whole brain region shown in panel 1100 after baseline subtraction and normalization by the average value of the subtracted curve. In order to be displayed together with the automatically detected arterial input function (FIG. 8), the normalized whole brain TDC has been scaled up by a factor of 100. A panel 1104 shows the smoothed fitted curve to the normalized whole brain TDC was found by deconvolution with the arterial input function. A panel 1106 shows the absolute difference between the normalized whole brain TDC and the fitted curve. The images may have significant z-axis movement relative to the rest of the images, for example, as shown by the differences of the skull representations.

FIG. 12 is a screen shot of a visual representation of image slices of a CTP study that shows patient motion in the Z-axis. according to some embodiments. Z-axis motion of the images of a slice from a CT Perfusion study. (A) The first image of the slice at time 0 sec. (B) Image at 2.8 sec. (C) Image at 36.4 sec. (D) Image at 104.0 sec. Motion led to differences in the skull within the dotted circles.

FIG. 13 is a screen shot of a visual representation of image slices of a CTP study showing the effect of z-axis motion on perfusion parameter maps of a CT Perfusion study according to some embodiments. The interface may be displayed on a display device. Effect of z-axis motion on perfusion parameter maps of a CT Perfusion Study. The CBF and $T_{max}$ maps with and without z-axis motion correction are shown together with the mean value within a circular region of interest within the stroke affected hemisphere and contralateral hemisphere. Panels 1300, 1302 show a CBF map without and with z-axis motion correction respectively displayed in the scale from 0-120 mL·min$^{-1}$. (100 g)$^{-1}$. Panels 1304, 1306 show $T_{max}$ map without and with z-axis motion correction respectively displayed in the scale from 0-16 seconds. The pixel values of the $T_{max}$ maps have been scaled up by a factor of 100 to facilitate the display of the maps, according to some embodiments. This may be screen shot of the functional maps from the same CTP study as FIG. 12 showing the effect with and without correction of head motion, for example.

FIG. 14 is a screen shot of visual representations of image slices from an application of time based infarct growth according to some embodiments. The visual representation illustrates an applied automated time based infarct growth paradigm on to perfusion maps and consequently validating them that may be displayed on an interface that may be displayed on display device 102. The screenshots may be generated by applying the automated time based infarct growth paradigm on to perfusion maps and consequently validating them. A panel 1400 shows a brain image with gray-matter segmentation and a panel 1402 shows another brain image with clustering to remove noise. The tool 22 may implement clustering techniques to provide an improved visual representation. A panel 1404 may show a "time is brain" paradigm to illustrate rates of irreversible infarct over time based on $T_{max}$, CBF and CBV values.

Figure 15:
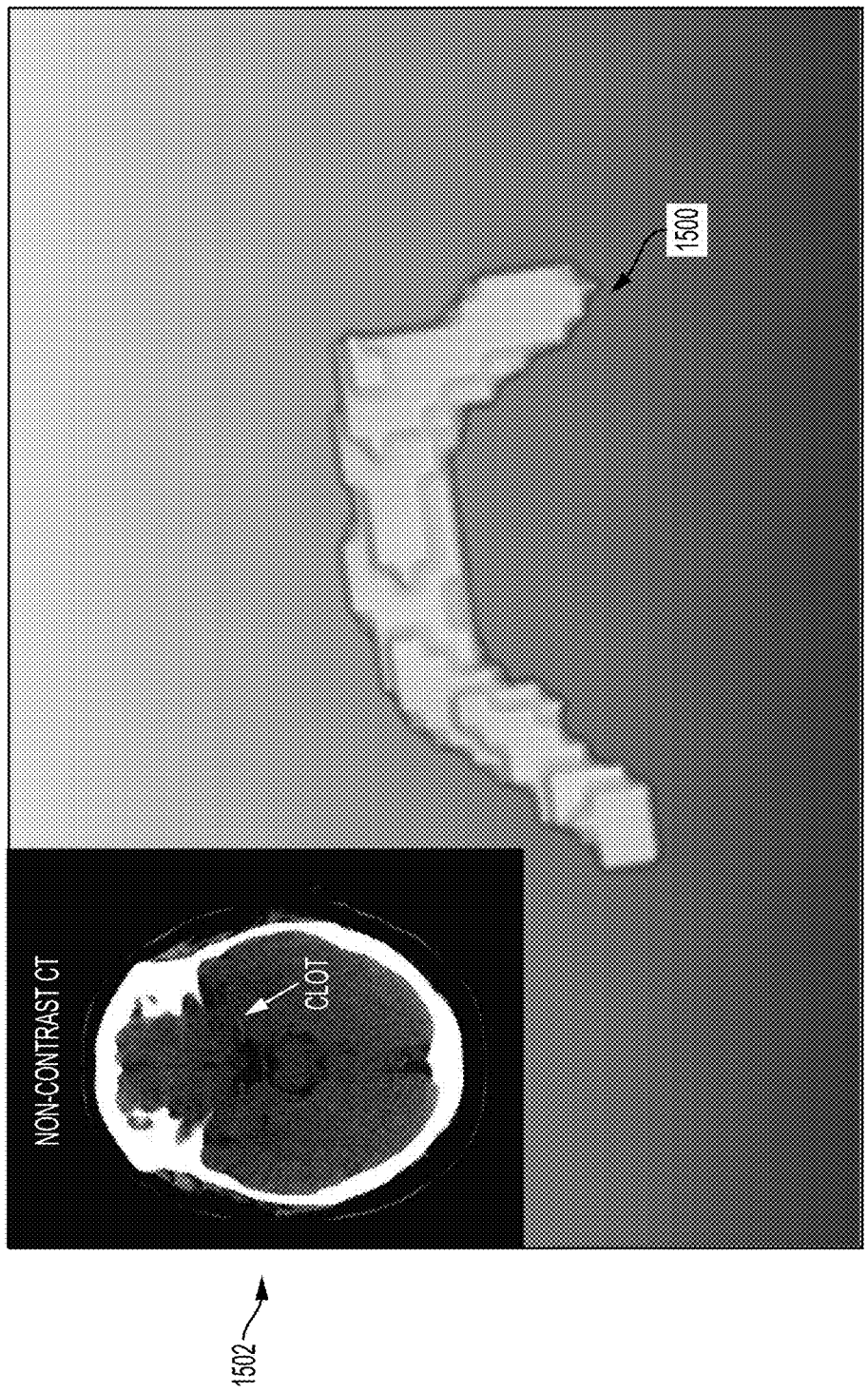
FIG. 15 is a screen shot of a visual representation of an example of a 3D clot segmentation from non-contrast CT (Left Inset) using proposed automated technique.

FIG. 15 is a screen shot of a visual representation of an example of a 3D clot segmentation 1500 from non-contrast CT representation (corner panel 1502) using proposed automated technique.

FIGS. 17 to 21 are schematics of example systems with the triage tool according to some embodiments.

Figure 17:
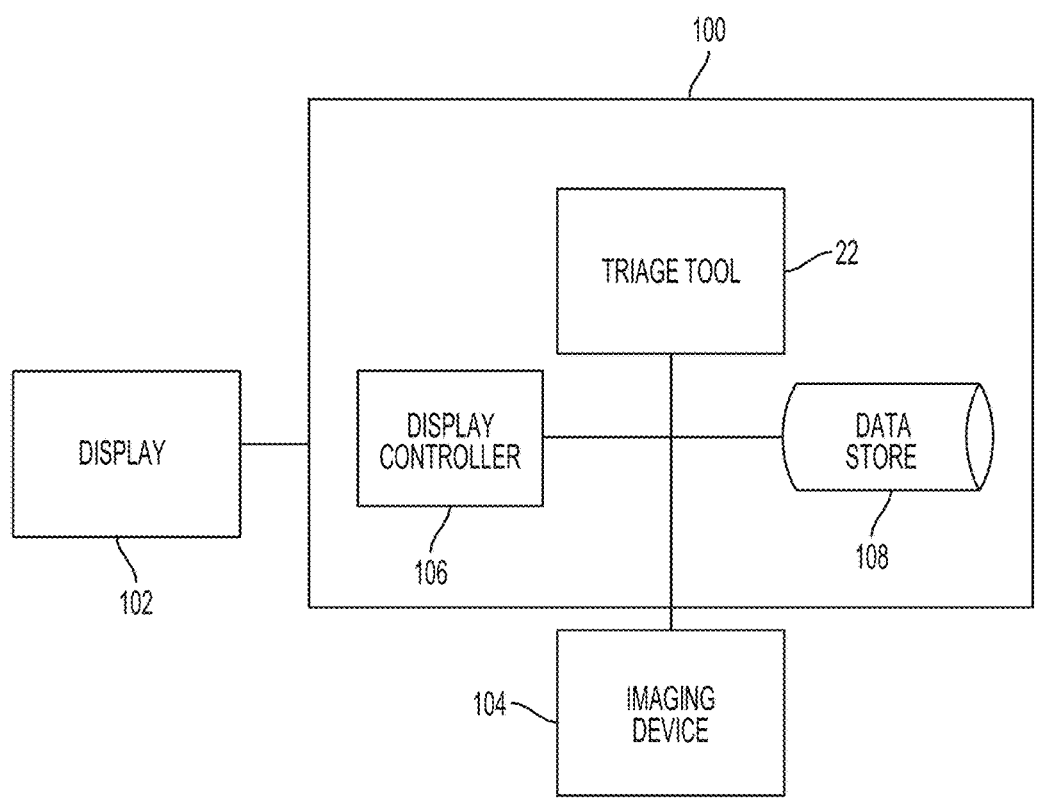
FIGS. 17 to 21 are schematics of example systems with the triage tool according to some embodiments.

FIG. 17 shows a system with a decision support tool 22 according to some embodiments. The example system includes the triage tool 22, an image data store 108, a display controller 106. The tool 22 receives brain scan or imaging data from an imaging device 104. Alternatively, the brain scan data may be received at data store 108 for storage and subsequent retrieval or access by tool 22. The display controller 106 control output of visual representations on a display 102.

For simplicity only one tool 22 is shown but system may include more tool 22 operable by users to access remote network resources and exchange data. The tool 22 may be the same or different types of devices. The tool 22 includes at least one processor, a data storage device (including volatile memory or non-volatile memory or other data storage elements or a combination thereof), and at least one communication interface (an example of which is shown in FIG. 16). The tool 22 components may be connected in various ways including directly coupled, indirectly coupled via a network, and distributed over a wide geographic area and connected via a network (which may be referred to as "cloud computing").

For example, and without limitation, the tool 22 may be a server, network appliance, set-top box, embedded device, computer expansion module, personal computer, laptop, personal data assistant, cellular telephone, smartphone device, UMPC tablets, video display terminal, and wireless hypermedia device or any other computing device capable of being configured to carry out the methods described herein.

The imaging device 104 may be a PACS for storage and access to medical images from multiple modalities and source machine types. The imaging device 104 may provide local storage, remote cloud based storage, or a combination thereof. Electronic images and reports may be stored and transmitted digitally via imaging device. The universal format for PACS image storage and transfer is DICOM. Further, imaging device 104 may manage non-image data, such as scanned documents. The imaging device 104 may include one or more imaging modalities such as CT and MR and a secured network for the transmission of patient and image data. The imaging device 104 may also workstations for interpreting and reviewing images and archives for the storage and retrieval of images and reports. Image device 104 may provide one or more of image creation, retrieval, distribution, and display.

The display controller 106 may receive configuration parameters to control the display and provision of the visual representation on the display. For example, the configuration parameters may receive a select set of output data to use for generation of the visual representation. The configuration parameters may include details regarding the display device and its capabilities. The display controller 106 may receive input from display 102 to reconfigure and update the rendering of the visual representations. The interface may include selectable indicia for receiving updates to configuration parameters for provisional to the display controller 106. The display controller 106 may provide any received configuration parameters to triage tool 22 as feedback to update the generation of output results, for example. Accordingly, the display controller 106 facilitates acquisition of feedback data and is involved in updating the visual representation based on the updated output results from the feedback. This facilitates the feedback loop as a visual representation may effectively illustrate the revised output and the impact of the feedback on the output.

Figure 18:
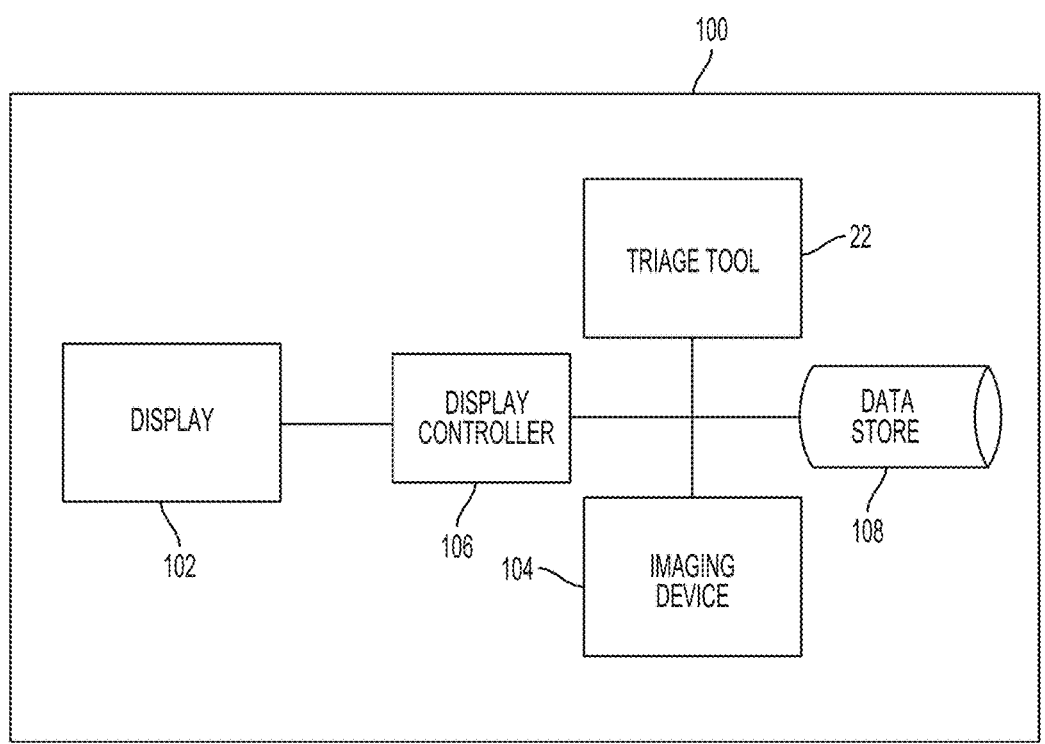

FIG. 18 is another example system with triage tool 22. In this example system, the triage tool 22 may be integrated as part of the imaging device 104 to process scans or images captured and generated by the imaging device 104 and stored in image data store 108. In this example system, the triage tool 22 may also be integrated as part of the display device 102 to display output and visual representations of the treatment protocol. The integrated interface between tool 22 and imaging device 104 may enable imaging modality specific configurations to be incorporated into tool 22 for improved processing.

Figure 19:
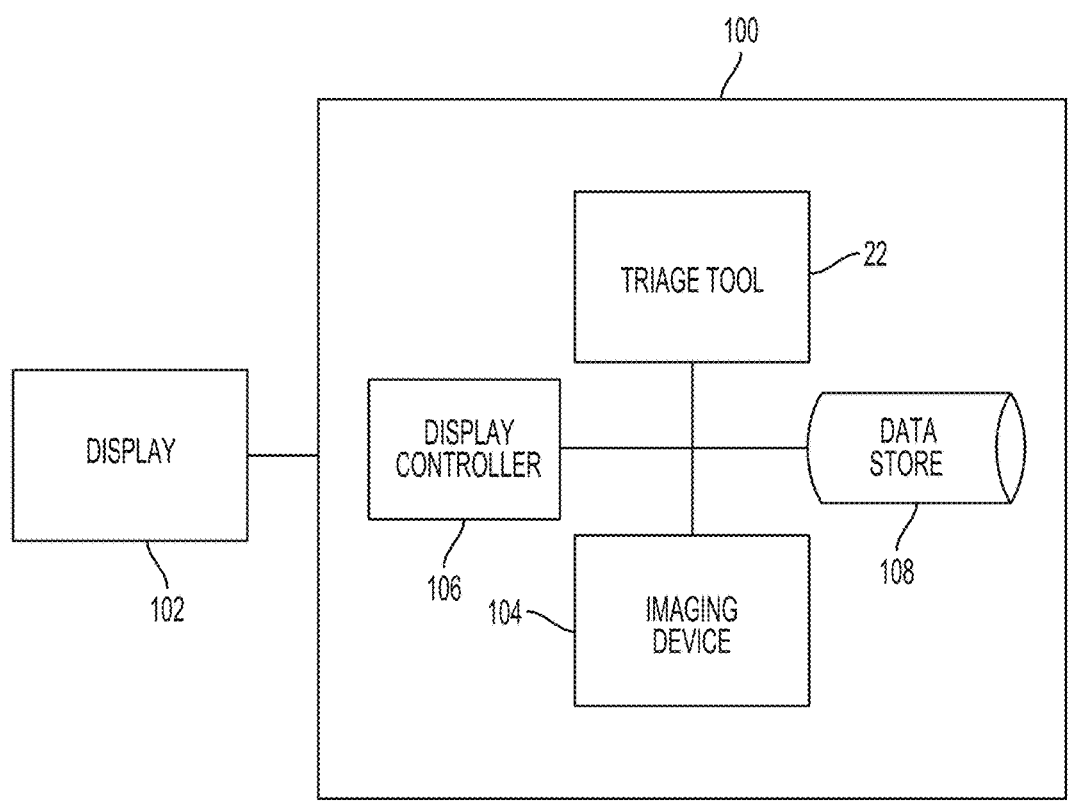

FIG. 19 is another example system with triage tool 22. In this example system, the triage tool 22 may be integrated as part of the imaging device 104 to process scans or images captured and generated by the imaging device 104 and stored in image data store 108. The display 102 may be a separate add on. This illustrates the versatility of tool 22 and the various system configurations it supports.

Figure 20:
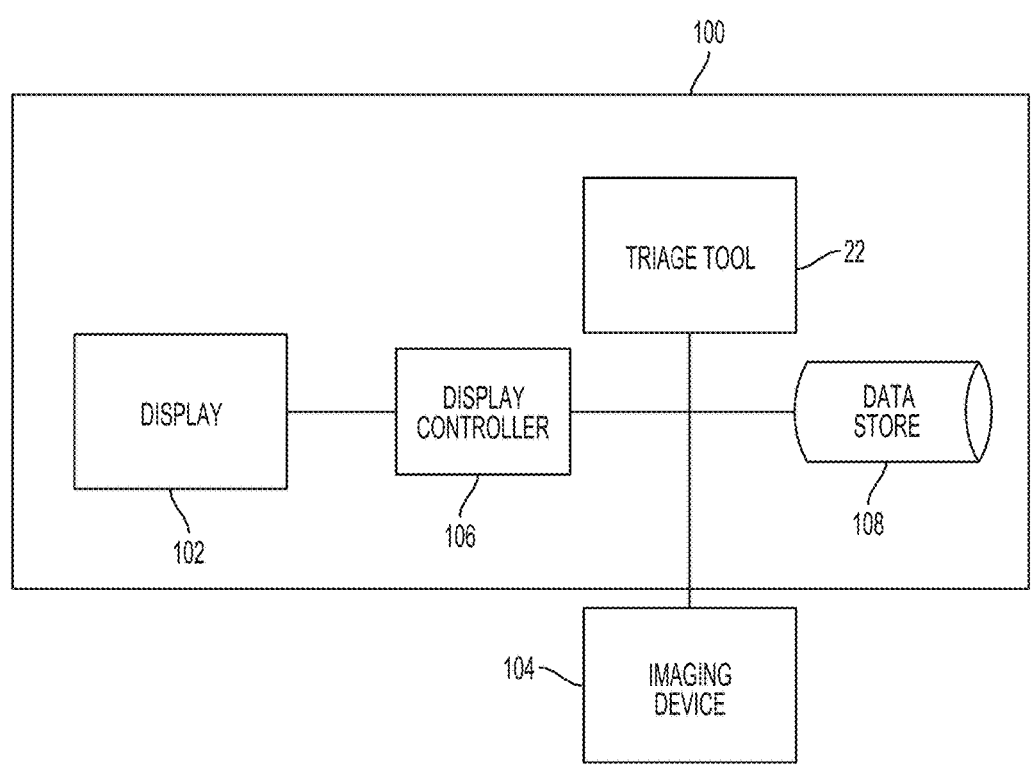

FIG. 20 is another example system with triage tool 22. In this example system, the triage tool 22 may be integrated as part of the display device 102 to display output data including visual representations of a treatment protocol, where the display controller 106 interfaces between the triage tool 22 and the display device 102. Although only one imaging device 104 is shown, tool 22 may integrate with multiple imaging devices 104 of different modalities. An interface may configure multiple connections to the different imaging devices 104.

Figure 21:
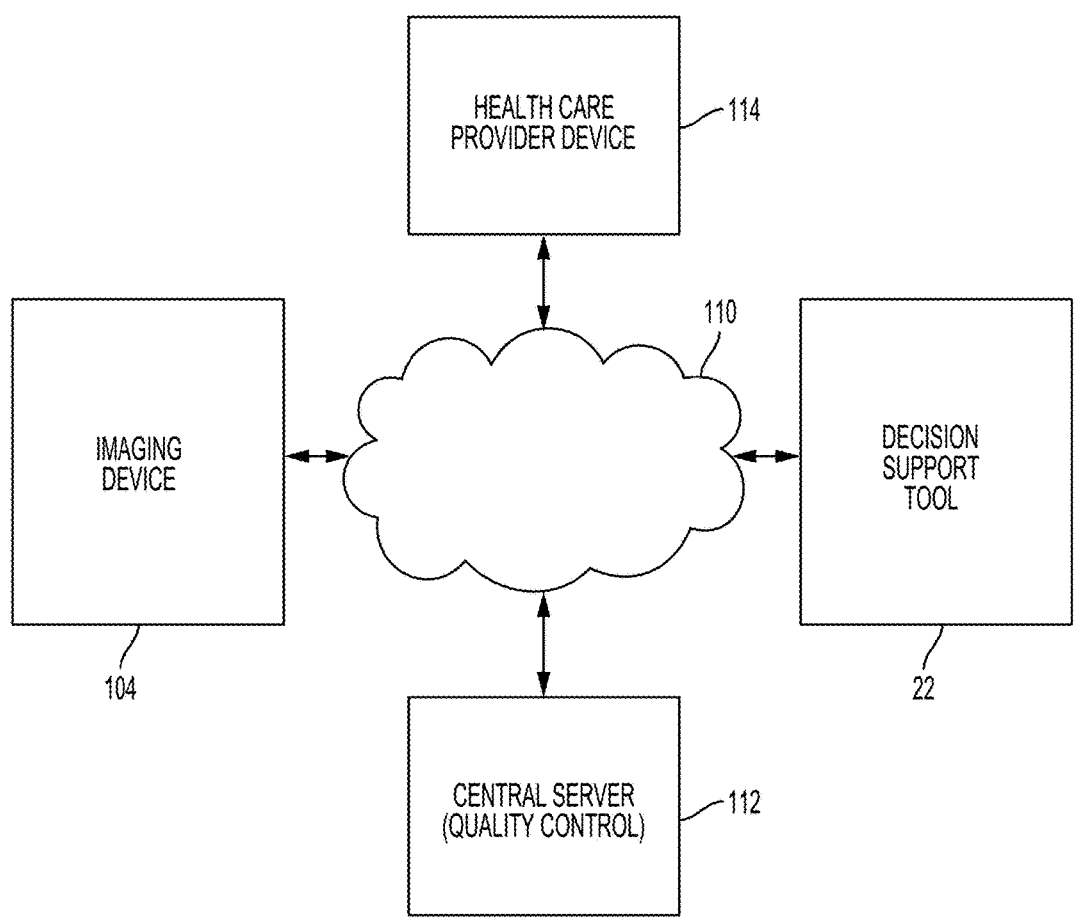

FIG. 21 is a schematic diagram of another system with triage tool 22 exemplary of an embodiment. In this example, the triage tool 22 connects to imaging device 104 via a network 110. The network 110 may include the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. WiMAX), SS7 signaling network, fixed line, local area network, wide area network, and others, including any combination of these. The triage tool 22 may receive imaging data from imaging device 104 via network 110, for example. The triage tool 22 may provide feedback and control commands to imaging device 104 via network 110. The triage tool 22 may transmit output results via network 110 to a display device or another processor for further data analysis or as a notification message. The network 110 may include PACS as described herein to access images.

The triage tool 22 may connect to a health care provider device 114 configured to display output results in an interface and receive control commands and feedback via the interface. The health care provider device 114 may be a workstation or a mobile device for example, to facilitate remote access of output results by health care provider. The triage tool 22 may connect to a central server 112 implementing quality control processes to validate data, receive feedback from different tools 22, and output results. Accordingly, a central server 112 may facilitate coordination of data and refinements across multiple tools 22.

The foregoing discussion provides many example embodiments. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A method for evaluating a patient suffering from acute stroke at a first treatment facility and providing time-based decision support to determine if transportation to a second treatment facility to effect reperfusion treatment at the second treatment facility would be effective for the patient, comprising the steps of:
   inputting patient clinical information and patient brain scan electronic images obtained at the first treatment facility into a processor;
   automatically generating, at the processor, a patient brain imaging profile using the patient clinical information and the brain scan electronic images, the imaging profile identifying a quantity and eloquence of brain tissue that is irreversibly infarcted, an estimated rate or quantity of patient brain tissue that will become irreversibly infarcted at a future time, a thrombus morphology associated with an estimate of a thrombus dissolving at the future time, and an estimated collateral blood flow;
   determining an estimated transport time to transfer the patient from the first treatment facility to the second treatment facility and an estimated treatment time for receiving reperfusion at the second treatment facility;
   dynamically determining, using the processor, a patient assessment profile by:
   processing the patient clinical information, the patient brain imaging profile, the estimated transport time from the first treatment facility to the second treatment facility, and the estimated treatment time at the second treatment facility to generate input data values;
   dynamically deriving weighting factors as an assessment of importance or relevance of the input data values and assigning the weighting factors to the input data values;
   deriving as time-based output data values for the patient assessment profile using the input data values and the weighting factors, the output data values being a probability of an expert treatment decision for transferring the patient from the first treatment facility to the second treatment facility and providing the reperfusion at the second treatment facility, a visual representation of the thrombus morphology, the estimated collateral blood flow, and an estimated quantity of brain tissue that will likely become irreversibly infarcted after the estimated transport time and/or the estimated treatment time;

outputting the time-based output values as clinical decision support information to trigger display on a display device, storage on a storage device, or transmission to another processor using a transmitter.

2. The method of claim 1, further comprising the step of:

determining or receiving a patient clinical data profile identifying an age or age range for the patient and a stroke severity, the stroke severity being determined from either a) a scale of mild, moderate, and severe or b) based on physician heuristics, and determining the patient assessment profile using the patient clinical data profile as input.

3. The method in claim 1, further comprising the step of determining one or more of:

the time elapsed since the onset of stroke symptoms as an additional input data values for the patient assessment profile;

the patient's pre-morbid status, general health, and co-morbidities as an additional input data values for the patient assessment profile;

the patient's advanced directives as an additional input data values forthe patient assessment profile; and current medications and/or medical history of patient that significantly influence decision making as an additional input data values for the patient assessment profile, including blood thinners and recent surgery.

4. The method of claim 1, further comprising the step of providing an imaging interface to connect to an imaging device to receive the brain scan image files, the imaging device selected from the group consisting of a scanner, a picture archiving communication system network, and a cloud image storage device, and wherein the patient brain electronic images may be of one or more imaging modalities selected from the group consisting of computed tomography (CT) scan, multi-phase computed tomography angiography (CTA), CT perfusion, magnetic resonance imaging (MRI), trans cranial doppler (TCD), ultrasound (US), electrical impedance plethysmography (EIS), and other imaging modalities.

5. The method of claim 1, wherein determining the estimated transport time from the first treatment facility to the second treatment facility and the estimated treatment time at the second treatment facility comprises the step of determining a required treatment for the patient and identifying one or more available treatment facilities based on available treatment services and equipment, available treatment times, available transportation type and the required treatment of the patient.

6. The method of claim 1, further comprising the steps of continuously updating the patient assessment profile using a feedback loop based on additional input data values including configurations for the current physician and health system, additional available patient and health system data, changing configurations for the physician and health care facility, updates for the one or more weighting factors, or control commands received from a display device displaying the visual representation.

7. The method of claim 1, further comprising the steps of constructing and continuously validating the patient assessment profile and the input data values using current and future clinical trial datasets.

8. The method of claim 1, further comprising the steps of constructing and continuously validating the patient assessment profile by receiving additional data and results on adjuvant therapies including neuro-protection and augmented thrombolytic techniques to change physician and health system heuristics.

9. The method of claim 1, further comprising the steps of receiving threshold data for a health care provider to update and customize the patient assessment profile, the weighting factors, and the input data values for the health care provider, health care data including a number of treatment centers providing endovascular treatment, staff availability, and other current health care metrics.

10. The method of claim 1, wherein determining the patient assessment profile further comprises the step of determining a rate of brain tissue death using collateral assessment on computed tomography angiography (CTA), computed tomography (CT) Perfusion, magnetic resonance imaging (MRI), trans cranial doppler (TCD), ultrasound (US), electrical impedance plethysmography (EIS), other brain and neurovascular imaging modality, or a combination thereof.

11. The method of claim 1, wherein the likelihood of the thrombus dissolving the over future time is determined by one or more techniques of measuring thrombus morphology such as a size of the thrombus, length of the thrombus, surface area of the thrombus, volume of the thrombus, and permeability to blood flow of the thrombus.

12. The method of claim 1, further comprising the step of determining a likelihood of the thrombus dissolving with administration of a thrombolytic drug using the thrombus morphology and the collateral blood flow.

13. The method of claim 1, wherein the output data values of the patient assessment profile indicates a comparison between risks of the administration of a thrombolytic drug and risks of endovascular treatment, the risks including a bleeding risk and other potentially major risks associated with thrombolytic drug administration and a treatment risk of not being able to administer the endovascular treatment or not successfully providing the endovascular treatment.

14. The method of claim 1, wherein the collateral blood flow is determined using mCTA, $T_0$ and $T_{max}$ values.

15. The method of claim 1, wherein the patient treatment protocol is selected from the group consisting of:

transferring the patient from the first treatment facility to the second treatment facility for treatment with endovascular therapy;

transferring the patient from the first treatment facility to the second treatment facility for direct treatment at the second treatment facility without additional or repeating brain scans;

retaining the patient at the first treatment facility for treatment with a thrombolytic drug; and retaining the patient at the first treatment facility.

16. The method of claim 1, further comprising the steps of:

receiving additional patient, clinical and imaging data for stroke patients;

updating the input data values using the additional patient, clinical and imaging data for stroke patients; and updating patient treatment protocol using machine learning and the additional patient data, health system data, the updating by applying additional weighting factors to the updated input data values.

17. The method of claim 1, wherein the treatment protocol indicates one or more of an automated prediction of thrombus lysability using the thrombus morphology, an automated quantitation of collateral status on a computed tomography perfusion (CTP) map and on multi-phase computed tomography angiography (CTA), and an automated assessment of severe hypoattenuation on non-contrast CT.

18. A decision support computing tool for evaluating a patient suffering from acute stroke at a first treatment facility and providing time-based decision support to determine if transportation to a second treatment facility to effect reperfusion treatment at the second treatment facility would be effective for the patient, comprising:
an image interface to receive patient brain electronic images at the first treatment facility;
a processor to:
receive patient clinical information;
generate a patient brain imaging profile using the patient brain scan electronic images and the patient clinical information, the imaging profile identifying a quantity and eloquence of brain tissue that is irreversibly infarcted, an estimated rate or quantity of patient brain tissue that will become irreversibly infarcted at a future time, a thrombus morphology associated with an estimate of a thrombus dissolving at the future time, and an estimated collateral blood flow;
determine an estimated transport time to transfer the patient from the first treatment facility to the second treatment facility and an estimated treatment time for receiving reperfusion at the second treatment facility; and
dynamically determining a patient assessment profile by:
processing the patient clinical information, the patient brain imaging profile, the estimated transport time from the first treatment facility to the second treatment facility, and the estimated treatment time to generate input data values;
dynamically deriving weighting factors as an assessment of importance or relevance of the input data values and assigning the weighting factors to the input data values;
deriving time-based output data values for the patient assessment profile using the input data values and the weighting factors, the output data values being a probability of an expert treatment decision for transferring the patient from the first treatment facility to the second treatment facility and providing the reperfusion at the second treatment facility, and a visual representation of the thrombus morphology, the estimated collateral blood flow, and an estimated quantity of brain tissue that will likely become irreversibly infarcted after the estimated transport time and/or the estimated treatment time; and
a display device to display the time-based output data values as clinical decision support information including the visual representation; and
a network interface to provide the time-based output data values to trigger transmission or storage.

19. An imaging system for evaluating a patient suffering from acute stroke at a first treatment facility and providing time-based decision support to determine if transportation to a second treatment facility to effect reperfusion treatment at the second treatment facility would be effective for the patient, comprising:
an imaging system to receive patient brain electronic images obtained at the first treatment center;
a decision support computing tool with a processor to:
receive patient clinical information;
generate a patient brain imaging profile using the patient brain scan electronic images and the patient clinical information, the imaging profile identifying a quantity and eloquence of brain tissue that is irreversibly infarcted, an estimated rate or quantity of patient brain tissue that likely will become irreversibly infarcted at a future time, a thrombus morphology associated with an estimate of a thrombus dissolving at the future time, and an estimated collateral blood flow;
determine an estimated transport time to transfer the patient from the first treatment facility to the second treatment facility and an estimated treatment time for receiving reperfusion at the second treatment facility; and
dynamically determining a patient assessment profile by:
processing the patient clinical information, the patient brain imaging profile, the estimated transport time from the first treatment facility to the second treatment facility, and the estimated treatment time at the second treatment facility to generate input data values;
dynamically deriving weighting factors as an assessment of importance or relevance of the input data values and assigning the weighting factors to the input data values;
deriving as time-based output data values for the patient assessment profile using the input data values and the weighting factors, the output data values being a probability of an expert treatment decision for transferring the patient from the first treatment facility to the second treatment facility and providing the reperfusion at the second treatment facility, and a visual representation of the thrombus morphology, the estimated collateral blood flow, and an estimated quantity of brain tissue that will likely become irreversibly infarcted after the estimated transport time and/or the estimated treatment time; and
an output device to output the time-based output data results as clinical decision support information to trigger display of the output data results on a display device, storage in a data storage device, or transmission for a transmitter.

* * * * *